(12) United States Patent
O'Halloran et al.

(10) Patent No.: US 12,167,855 B2
(45) Date of Patent: Dec. 17, 2024

(54) DEVICE FOR IMPLANTATION IN A LEFT ATRIAL APPENDAGE OF THE HEART

(71) Applicant: NATIONAL UNIVERSITY OF IRELAND, GALWAY, Galway (IE)

(72) Inventors: Tony O'Halloran, County Galway (IE); John Thompson, Dublin (IE)

(73) Assignee: University of Galway, Galway (IE)

( * ) Notice: Subject to any disclaimer, the term of this patent is extended or adjusted under 35 U.S.C. 154(b) by 0 days.

(21) Appl. No.: 17/284,333

(22) PCT Filed: Oct. 11, 2019

(86) PCT No.: PCT/EP2019/077669
§ 371 (c)(1),
(2) Date: Apr. 9, 2021

(87) PCT Pub. No.: WO2020/074738
PCT Pub. Date: Apr. 16, 2020

(65) Prior Publication Data
US 2021/0369283 A1  Dec. 2, 2021

(30) Foreign Application Priority Data
Oct. 11, 2018 (EP) .................................... 18199970

(51) Int. Cl.
*A61B 17/12* (2006.01)
*A61B 17/00* (2006.01)
*A61B 18/00* (2006.01)

(52) U.S. Cl.
CPC .. *A61B 17/12122* (2013.01); *A61B 17/12172* (2013.01); *A61B 2017/00035* (2013.01);
(Continued)

(58) Field of Classification Search
CPC ........ A61B 17/12122; A61B 17/12172; A61B 2017/00035; A61B 2017/00084;
(Continued)

(56) References Cited

U.S. PATENT DOCUMENTS

| 4,909,789 A | 3/1990 | Taguchi et al. |
| 5,573,530 A | 11/1996 | Fleury et al. |

(Continued)

FOREIGN PATENT DOCUMENTS

| DE | 10328445 A1 | 1/2005 |
| EP | 0800781 A2 | 10/1997 |

(Continued)

OTHER PUBLICATIONS

International Search Report and Written Opinion in corresponding Application No. PCT/EP2019/077669, dated Feb. 5, 2020 (10 pages), pp. 1-10.

*Primary Examiner* — Sarah W Aleman
*Assistant Examiner* — Mikail A Mannan
(74) *Attorney, Agent, or Firm* — Bookoff McAndrews, PLLC

(57) ABSTRACT

A device for implantation in a left atrial appendage of the heart comprises docking station comprising a radially expansible element that is adjustable between a contracted orientation suitable for transluminal delivery and a deployed orientation configured to anchor within the left atrial appendage and fluidically isolate the left atrial appendage from the left atrium, the docking station also includes a recessed socket accessible from the left atrium through an opening, and a closure coving the opening. A modular active element is configured for detachable engagement within the recessed socket of the docking station. The modular active element comprises a treatment element configured to electrically stimulate heart tissue, thermally stimulate heart (Continued)

tissue, electroporate heart tissue, or deliver a substance into heart tissue or a chamber of the heart, or a sensing element configured to detect a parameter selected from temperature, pressure, electrical signal, heart rate, or respiratory rate.

19 Claims, 15 Drawing Sheets

(52) U.S. Cl.
CPC ............... *A61B 2017/00084* (2013.01); *A61B 2017/00893* (2013.01); *A61B 2017/12095* (2013.01); *A61B 2018/00351* (2013.01); *A61B 2018/00613* (2013.01); *A61B 2018/00839* (2013.01); *A61B 2560/0219* (2013.01)

(58) Field of Classification Search
CPC ........... A61B 2017/00893; A61B 2017/12095; A61B 2018/00351; A61B 2018/00613; A61B 2018/00839; A61B 2560/0219
See application file for complete search history.

(56) References Cited

U.S. PATENT DOCUMENTS

| | | | |
|---|---|---|---|
| 6,454,775 | B1 | 9/2002 | Demarais et al. |
| 6,652,548 | B2 | 11/2003 | Evans et al. |
| 8,528,147 | B2 | 9/2013 | Larsson et al. |
| 2004/0219028 | A1 | 11/2004 | Demarais et al. |
| 2007/0276201 | A1* | 11/2007 | Lee ..................... A61B 5/0205 600/301 |
| 2014/0364941 | A1* | 12/2014 | Edmiston ......... A61B 17/12122 623/2.11 |
| 2016/0073960 | A1* | 3/2016 | Jung .................... A61B 5/6858 600/374 |
| 2018/0250014 | A1 | 9/2018 | Melanson et al. |
| 2019/0365385 | A1* | 12/2019 | Gorochow ....... A61B 17/12168 |

FOREIGN PATENT DOCUMENTS

| | | |
|---|---|---|
| WO | 0187168 A1 | 11/2001 |
| WO | 2013109756 A2 | 7/2013 |
| WO | 2014141226 A1 | 9/2014 |
| WO | 2016202708 A1 | 12/2016 |
| WO | 2017157316 A1 | 9/2017 |

* cited by examiner

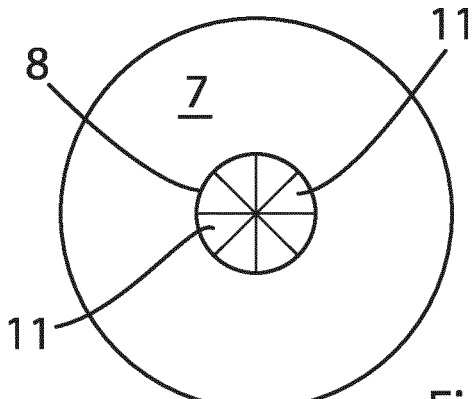 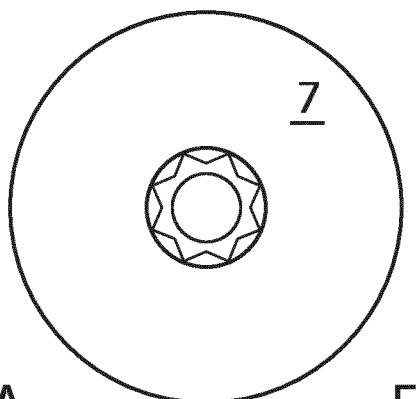
Fig. 2A  Fig. 2B
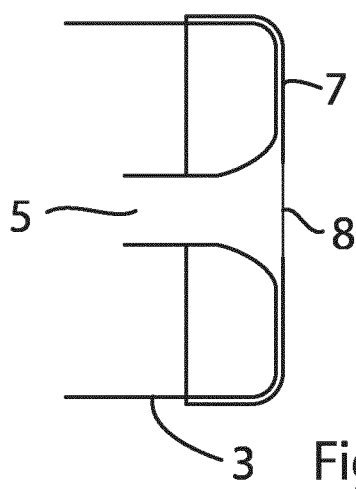 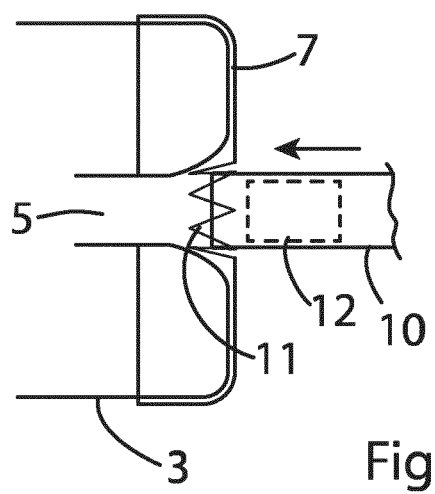
Fig. 2C  Fig. 2D
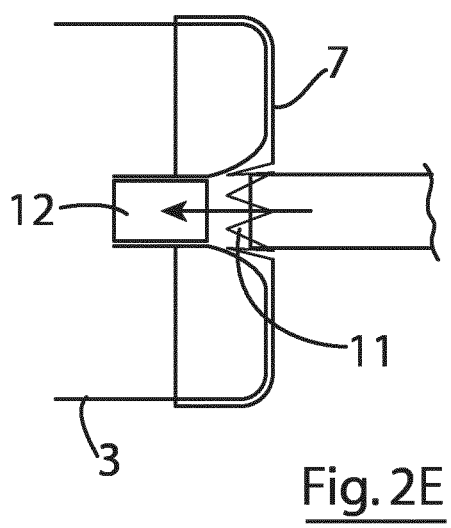 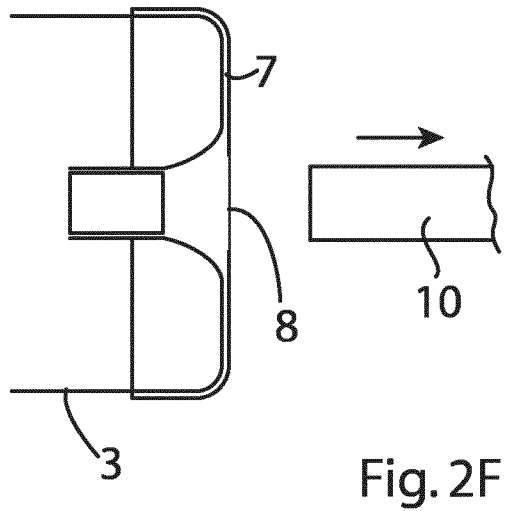
Fig. 2E  Fig. 2F

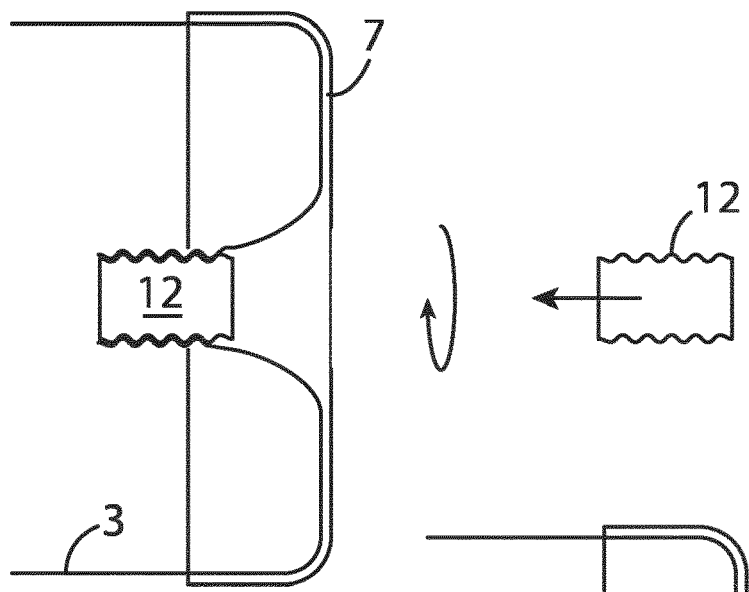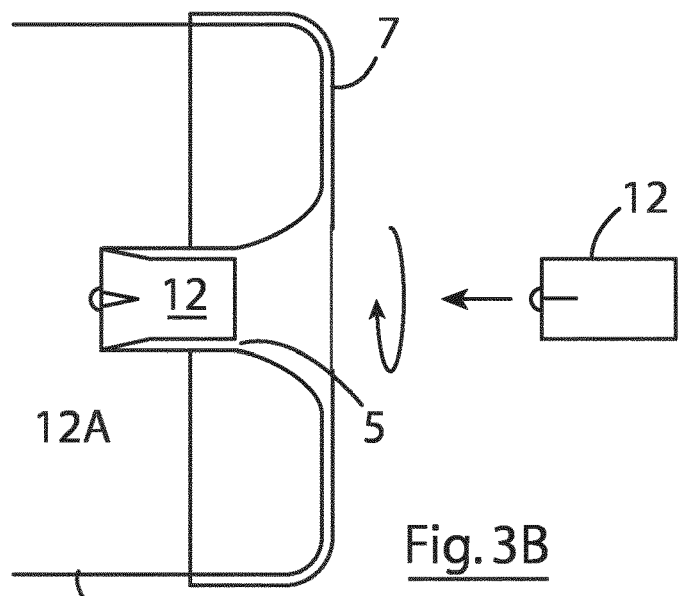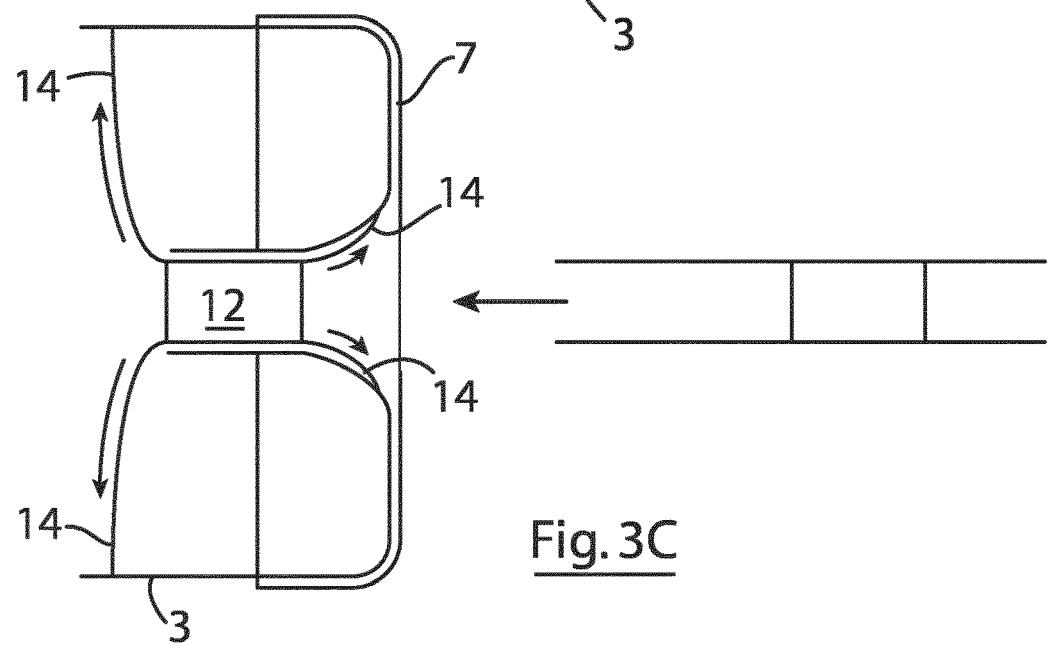

DEVICE FOR IMPLANTATION IN A LEFT ATRIAL APPENDAGE OF THE HEART

CROSS-REFERENCE TO RELATED APPLICATION(S)

This patent application is the U.S. National Phase Entry under 35 U.S.C. § 371 of International Application No. PCT/EP2019/077669, filed on Oct. 11, 2019, which claims priority to EP application Ser. No. 18/199,970.7, filed on Oct. 11, 2018.

FIELD OF THE INVENTION

The present invention relates to a device for implantation in a left atrial appendage of the heart. Also contemplated are methods of treatment or diagnosis that employ the device, in particular diagnosis of heart function

BACKGROUND TO THE INVENTION

Heart disease is a major issue for the population, and devices aimed at in-situ treatment and monitoring of the heart have been developed during the last 20 years. Space is extremely limited within the beating heart, and this provides a major challenge for the development of safe and effective in-situ heart implants.

Medical implant devices for the left atrial appendage (LAA) of the heart are known from the literature, and generally comprise a catheter and a radially expandable member disposed on a distal end of the catheter configured for deployment in the ostium of the LAA and fluidically isolating the LAA from the heart. These devices are generally operably connected to an external controller through the catheter, and operable to treat the tissue of the LAA with a view to changing the electrical properties of the LAA and ultimately electrically isolate the LAA from the heart tissue as a means of inhibiting or preventing atrial fibrillation. Some of these devices also include sensors which can sense a parameter of the tissue of the LAA. An exemplary device is described in WO2016/202708.

It is an object of the invention to overcome at least one of the above-referenced problems.

SUMMARY OF THE INVENTION

The Applicant has realised that the LAA can provide an additional space to accommodate a heart treatment/sensing device, and that by safely and definitively walling off the LAA using an LAA implant, it is possible to create additional space, within the heart but isolated from the heart. This space can then be employed as a receptacle for treatment or monitoring apparatus' or as a doorway to access the outer surface of heart from within the heart or access the inner aspect of the heart from outside the heart.

The present invention addresses the need for a heart monitoring/treatment device that can be safely implanted in the heart without negatively affecting heart function, and that is configured for modular adjustment. The device comprises two main components, a docking station designed for implantation within the left atrial appendage (LAA) of the heart, where it is anchored to the wall of the LAA, and a modular active element that is designed for detachable engagement in a recessed conduit (socket) formed in the docking station. The modular active element may be a treatment device or a sensing device, and can be removed from the docking station while it is in-situ in the heart and replaced with a different modular active element (for example replacement of a tissue ablation module with a heart parameter sensor), or replaced with a new version of the same modular active element, or the same modular active element with a new battery. The treatment or sensing device may be configured for a treatment or sensing operation applied to the LAA, the heart, a chamber of the heart (for example the left atrium), or the blood passing through the heart. The modular active element and recessed conduit and configured for detachable engagement to allow detachment and retraction of the modular active element, and re-attachment of the same or a different modular active element, while the docking station remains in-situ in the LAA of the heart. The invention thus provides a safe and convenient means for treating, or monitoring the condition of, the heart. The recessed socket may extend through the docking station, allowing part of the modular active element, for example a treatment or sensing device, access to the occluded LAA.

In a first aspect, the invention provides a device for implantation in a body lumen, for example the left atrial appendage of the heart, comprising a docking station comprising a radially expansible element that is adjustable between a contracted orientation suitable for transluminal delivery and a deployed orientation configured to lodge within the left atrial appendage (and preferably fluidically isolate the left atrial appendage from the left atrium). In one embodiment, the docking station comprises a recessed socket accessible from the left atrium. The device typically includes a modular active element configured for detachable engagement within the recessed socket of the docking station.

In one embodiment, a proximal face of the recessed socket comprises a closure configured to prevent fluidic access into the recessed socket. Various forms of closures are described herein, including self-closing closures and pierceable closures.

In one embodiment, the at least one of the modular active elements and docking station comprises a magnet (or is magnetised and) configured to guide the modular active element into the recessed socket.

The modular active element generally comprises a treatment element or a sensing element. The treatment or sensing element may be radially expandable. The sensing element may be configured to detect any parameter, examples include a parameter selected from temperature, pressure, pH, electrical signal, heart rate, or respiratory rate.

In one embodiment, the modular active element is a treatment element configured to electrically stimulate the heart, ablate heart tissue (by any means, including thermal, electrical, radiation, physical or chemical ablation), or deliver a substance into the heart, heart wall or the bloodstream.

In one embodiment, the treatment element comprises thermal and non-thermal energy delivery element such as RF, reversible and irreversible electroporation cryogenic element or capacitive coupling. The element may be an electrode or an array of electrodes. The cryogenic element may be a radially expandable balloon.

In one embodiment, the treatment element or sensing element is configured for adjustment between a retracted delivery configuration and a deployed active configuration. Generally, in these embodiments, the treatment or sensing element is disposed towards a distal end of the modular active element, and is configured for deployment distally of the recessed socket.

In one embodiment, the docking station and modular active element are configured for electrical connection when the modular active element is operably engaged within the recessed socket. In one embodiment, the docking station is configured to provide electrical connection between the modular active element and surrounding tissue through the radially expansible element.

In one embodiment, the recessed socket extends fully through the docking station, providing access to the occluded LAA when the docking station has been deployed.

In one embodiment, the modular active element is dimensioned to engage fully within the recessed socket. In one embodiment the modular active element is dimensioned to engage within the recessed socket to close the recessed socket. This prevents fluid flow from the heart into the LAA through the recessed socket when the aperture has been opened, for example when the recessed socket closure comprises a pierceable membrane or cover.

In one embodiment, the modular active element is configured to engage within the recessed socket with a proximal part of the modular active element disposed proximally of the recessed socket and/or a distal part of the modular active element disposed distally of the recessed socket. In one embodiment, the modular active element is configured to sit within the recessed socket with a proximal part extending into the left atrium. In one embodiment, the proximal part extending into the left atrium comprises a treatment or sensing element.

In one embodiment, the modular active element is dimensioned to fit within the heart. In one embodiment, the modular active element is dimensioned to fit within the left atrium (including the left atrial appendage). In one embodiment, the modular active element is dimensioned to fit within the left atrial appendage.

In one embodiment, the recessed conduit is configured for radial expansion upon receipt of a modular active element. In this embodiment, a modular active element may have a diameter that is greater than a diameter of the recessed conduit. Insertion of the modular active element into the recessed socket subjects the recessed socket to tensile forces forcing it to expand radially. The socket may be formed of a resiliently deformable material, for example a suitable elastic polymer or an expansible mesh, configured to assume its original size when the modular active element is removed. Alternatively, the socket may be tubular, having adjacent but unconnected longitudinal sections that abut longitudinally when the socket is not expanded, but separate when the socket is expanded. The modular active element may have distal end that tapers inwardly (i.e. funnel shaped). This allows the distal end of the modular active element to be inserted into the recessed socket prior to radial expansion, whereby further insertion of the element into the socket effects radial expansion of the socket.

In one embodiment, the closure for the recessed socket comprises a mesh cover which typically fluidically isolated the left atrium from the LAA when the device is deployed in the LAA. In one embodiment, the mesh comprises a self-closing aperture.

In one embodiment, the closure comprises a pierceable membrane cover.

In one embodiment, the self-closing closure comprises a dilatable valve.

In one embodiment, the closure is configured to promote epithelial cell proliferation In one embodiment, the self-closing closure comprises an openable flap and associated biasing means for biasing the flap into a closed position. In one embodiment, the biasing means comprises a spring element adhered to the flap, for example a hinged spring as disclosed herein.

In one embodiment, the radially expansible element is a radially expansible cage. In one embodiment the recessed socket is a conduit that extends axially at least partly, and in one embodiment fully, into and through the radially expansible cage or element. In one embodiment, the radially expansible element comprises proximal part having a substantially toroidal shape and comprising an opening of the recessed socket, a cover for the recessed socket, and a distal part that is substantially cylindrical.

In one embodiment, the modular active element and recessed socket are configured for inter-engagement when the modular active element is fully received in the recessed socket In one embodiment, the modular active element and recessed socket are configured for screw-fit detachable engagement.

In one embodiment, the modular active element and recessed socket are configured for interference-fit detachable engagement.

In one embodiment, the modular active element comprises a radially expansible anchor configured to anchor the modular active element in the recessed socket upon engagement (or as a means of engagement). In one embodiment, the radially expandable anchor is inflatable.

In one embodiment, the modular active element comprises a distal radially expansible anchor configured to deploy distally of the conduit or radially expansible element when the modular active element is engaged with the recessed socket and/or a proximal radially expansible anchor configured to deploy proximally of the conduit or radially expansible element when the modular active element is engaged with the recessed socket In one embodiment, the modular active element comprises an inductor.

In one embodiment, the inductor comprises an inductor coil, that is optionally adjustable between a contracted orientation suitable for transluminal delivery and a deployed radially expanded orientation.

In one embodiment, the inductor coil is disposed on a distal end of the modular active element and configured for deployment distally of the recessed conduit.

In one embodiment, the modular active element comprises a resonant power circuit configured with a plurality of coils adapted to provide a desired Q factor greater than or equal to 0.5

In one embodiment, the modular active element comprises a capacitor paired with an inductor to provide a first LC circuit.

In one embodiment, the modular active element comprises a RC circuit operably connected to a DC regulator and adapted to provide a steady state current to the circuit.

In one embodiment, the modular active element comprises a second LC circuit positioned external to the modular active element adapted to provide a magnetic flux to power the LC circuit, In one embodiment, a proximal end of the modular active element comprises an anchor formation configured for engagement with a retraction snare.

In one embodiment, the modular active element is configured to remain attached to its delivery catheter during use. The delivery catheter may comprise control elements for the modular active element including power supply means and data relay means. The catheter and modular active element may be configured for disengagement from the docking station and transluminal withdrawal together. The modular active element may be configured for detachment from the delivery catheter and the catheter configured for attachment of a replacement modular active element. The catheter and replacement modular active element may be transluminally delivered to the docking station and the modular active element operably engaged within the recessed socket.

In one embodiment, the cover at the distal end of the docking station comprises a network of electrode-receiving conduits that extend radially from a centre of the cover to a periphery of the cover. Electrodes disposed at a distal end of a delivery catheter are threaded through the conduits, which guide the distal end of the electrodes to the periphery of the cover that in use will be adjacent the wall of the LAA. In one embodiment, the circumference of the tissue-engaging part of the cover comprises a plurality of apertures configured to expose the distal end of the electrodes to the wall of the LAA. The catheter and electrodes are configured for detachment from the docking station, and withdrawal leaving the docking station in-situ.

In one embodiment, the radially expansible element comprises one or a plurality of brush members configured to engage tissue upon deployment of the radially expansible element. The brush helps affix the element to the tissue upon deployment, and also form a fluidically tight seal against the tissue. For example, the radially expansible element may be a cage formed from wires, and at least one of the wires may comprise a brush member. The term "brush member" as employed herein generally means a spine and a plurality of bristles coupled to the spine, the bristles extending outwardly, generally radially outwardly, from the spine. The bristles may have a axial, circumferential or helical arrangement. Brush members, and method for their manufacture, are described in the following documents: U.S. Pat. No. 8,528,147; EP0800781, and DE10328445. The bristles may be porous, which helps with tissue integration. The pores can be formed during extrusion, or post formation by means of cutting or lasering.

The invention also provides a system comprising a device of the invention and a delivery catheter to transluminally deliver a modular active element to the recessed conduit of the docking station. In one embodiment, the delivery catheter is configured to receive the modular active element (typically within a distal end of the catheter), transluminally deliver the modular active element to the docking station, and dispense the modular active element from a distal end of the delivery catheter partially or fully into the recessed socket of the docking station. In one embodiment, the delivery catheter comprises an inner element configured for detachable attachment with a proximal ed of the modular active element and axial movement relative to the catheter. In one embodiment, the inner element is configured to rotate the modular active element about a longitudinal axis of the catheter.

In one embodiment, the invention provides a device for occlusion of a body lumen comprising an implantable occlusion apparatus operably attached to an elongated catheter member configured for transluminal delivery and deployment of the occlusion apparatus in the body lumen, the occlusion apparatus comprising a radially expansible element detachably attached to the elongated catheter member, and adjustable between a contracted orientation suitable for transluminal delivery and a deployed orientation configured to occlude the body lumen, wherein the radially expansible element comprises one or a plurality of brush members configured to engage tissue upon deployment of the radially expansible element. In one embodiment, the device comprises an energy delivery element configured to deliver energy to surrounding tissue to heat the tissue. In one embodiment, the device comprises a sensor configured to detect a parameter of the wall of the body lumen. In one embodiment the energy delivery element and sensor are optionally configured for axial movement independently of the radially expansible element whereby, in use, the energy delivery element and sensor can be transluminally retracted leaving the radially expansible element in-situ occluding the body lumen.

The invention also relates to a method comprising the steps of:
transluminally delivering a device of the invention to the left atrial appendage of a heart of a subject;
deploying the device to anchor the device in the left atrial appendage;
actuating the modular active element to perform a first operation in-situ in the heart;
after a period of time detaching the modular active element from the docking station and withdrawing the modular active element from the subject transluminally;
transluminally delivering a replacement modular active element to the heart of the subject;
inserting the replacement modular active element into the recessed conduit of the docking station and into engagement with the recessed conduit; and
actuating the modular active element to perform a second operation in-situ in the heart.

In one embodiment, the first and second operation are each, independently, a treatment operation (i.e. LAA tissue ablation, drug or gene therapy delivery) or a sensing operation (i.e. detection of electrical signalling, pressure or temperature in the LAA). The first and second operations may be different or the same. The modular active element and replacement modular active element may be different or the same. For example, one may comprise a treatment element and one may comprise a sensing element, or they both may comprise a treatment or sensing element.

In one embodiment, the step of detaching the modular active element from the docking station and withdrawing the modular active element from the subject transluminally employs a catheter having an outer part configured to abut a proximal face of the radially expansible element surrounding the opening of the recessed socket and an inner part configured for axial movement into the recessed socket and engagement with a proximal end of the modular active element. Typically, the inner part of the catheter has a piercing tip configured to pierce the cover covering the opening of the recessed socket. Suitably, the outer part of the catheter comprises a magnet to facilitate correctly locating the outer part against the proximal face of the radially expansible element.

In one embodiment, the replacement modular active element comprises a radially expansible anchor configured to anchor the replacement modular active element in the recessed socket upon engagement, wherein the method includes a step of deploying the anchor after the replacement modular active element has been inserted into the recessed conduit. In one embodiment, the radially expandable anchor is inflatable.

The method of the invention may be a method of occluding, devascularising or electrically isolating, the LAA in which the modular active element comprises a tissue ablation element for ablation of tissue directly (in which parts of the element are configured to engage the LAA tissue) or indirectly (in which the tissue ablation element is configured to deliver ablation energy to the tissue by means of the radially expansible element.

The invention also provides a kit of parts comprising a device according to the invention and at least one (i.e. 1, 2, 3, 4, 5) replacement modular active element.

In one embodiment, the modular active element is a tissue ablation device, and the replacement modular active element is selected from a treatment device or a sensing device.

In one embodiment, the kit includes a catheter having an outer part configured to abut a proximal face of the radially expansible element surrounding the opening of the recessed socket and an inner part configured for engagement with a proximal end of the modular active element, and optionally configured for axial movement into the recessed socket.

In one embodiment, the inner part of the catheter has a piercing tip configured to pierce the cover covering the opening of the recessed socket.

In another aspect, the invention provides a device for implantation in a left atrial appendage of the heart, comprising:
 a docking station comprising a radially expansible element that is adjustable between a contracted orientation suitable for transluminal delivery and a deployed orientation configured to anchor within the left atrial appendage and fluidically isolate the left atrial appendage from the left atrium, a recessed socket accessible from the left atrium through an opening, and a closure covering the opening; and
 a modular active element configured for detachable engagement within the recessed socket of the docking station, in which the modular active element comprises an inductor.

In one embodiment, the inductor comprises an inductor coil, that is optionally adjustable between a contracted orientation suitable for transluminal delivery and a deployed radially expanded orientation. In one embodiment, the inductor coil is disposed on a distal end of the modular active element and configured for deployment distally of the recessed conduit.

In another aspect, the invention provides a device for implantation in a left atrial appendage of the heart, comprising:
 a docking station comprising a radially expansible element that is adjustable between a contracted orientation suitable for transluminal delivery and a deployed orientation configured to anchor within the left atrial appendage and fluidically isolate the left atrial appendage from the left atrium, a recessed socket accessible from the left atrium through an opening, and a closure covering the opening; and
 a modular active element configured for detachable engagement within the recessed socket of the docking station, in which the modular active element comprises a resonant power circuit configured with a plurality of coils adapted to provide a desired Q factor greater than or equal to 0.5

In another aspect, the invention provides a device for implantation in a left atrial appendage of the heart, comprising:
 a docking station comprising a radially expansible element that is adjustable between a contracted orientation suitable for transluminal delivery and a deployed orientation configured to anchor within the left atrial appendage and fluidically isolate the left atrial appendage from the left atrium, a recessed socket accessible from the left atrium through an opening, and a closure covering the opening; and
 a modular active element configured for detachable engagement within the recessed socket of the docking station, in which the modular active element comprises a capacitor paired with an inductor to provide a first LC circuit.

In one embodiment, the modular active element comprises a RC circuit operably connected to a DC regulator and adapted to provide a steady state current to the circuit.

In one embodiment, the modular active element comprises a second LC circuit positioned external to the modular active element adapted to provide a magnetic flux to power the LC circuit, Other aspects and preferred embodiments of the invention are defined and described in the other claims set out below.

BRIEF DESCRIPTION OF THE FIGURES

FIG. 1A shows the docking station with a mesh cover covering the proximal end of the cage and FIG. 1B shows the docking station with the cover removed for clarity. FIG. 1B also shows the distal end of a catheter attached to the docking station. FIGS. 1C and 1D are side views of the docking station, showing the re-closable aperture in an open (FIG. 10) and closed (FIG. 1D) configuration. FIGS. 1E and 1F are end views of the docking station.

FIGS. 2A and 2B show a cover for the proximal end of the docking station having re-closable aperture in the form of a polymeric valve in a closed (FIG. 2A) and open (FIG. 2B) configuration.

FIGS. 2C to 2F are sectional side views of the docking station showing the valve in a closed configuration (FIG. 2C) and open configuration with a catheter projecting through the valve (FIG. 2D), a modular active element being delivered into the recessed socket (FIG. 2E), and the catheter removed (FIG. 2F) and the valve closed.

FIG. 7 illustrates a tissue ablation modular active element.

DETAILED DESCRIPTION OF THE INVENTION

Figure 1A:
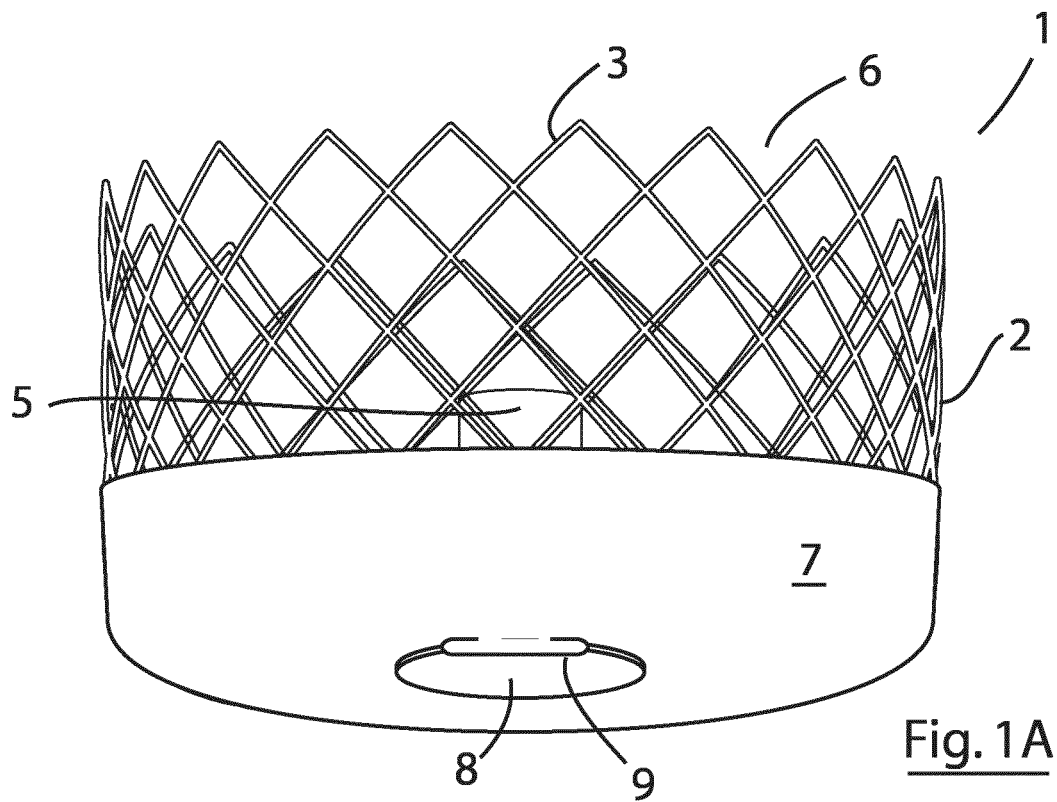
FIGS. 1A to 1F: A docking station of the invention in a deployed configuration having a radially expandable cage with a proximal end of substantially toroidal shape and recessed conduit, and a distal end having a cylindrical shape, and showing the reclosable aperture to facilitate removal and insertion of a modular active element.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

"Transluminal delivery" means delivery of the device to a target site (for example the heart) through a body lumen, for example delivery through an artery or vein. In one embodiment, the device of the invention is advanced through an artery or vein to the left atrium of the heart and at least partially in the LAA.

"Docking station" refers to a part of the device of the invention that is anchored inside an individual's heart inside the left atrial appendage (LAA), and that remains in the LAA allowing the modular active elements to be replaced periodically. For example, the modular active element may be a battery powered sensor that requires the batteries to be replaced periodically. The docking station generally comprises a radially expansible element that deploys to lodge the device in the LAA, and generally comprises a recessed conduit (socket) accessible from the left atrium and configured for detachable engagement with a modular active element. In one embodiment, the radially expansible element comprises an expandable cage having a conduit, typically an axial conduit. The conduit typically has an opening disposed on a proximal side of the docking station to allow access into the conduit from the left atrium. The conduit is generally covered by a cover, typically having a reclosable aperture configured to allow a modular active element access into the conduit and to close after the element has been placed in the conduit (i.e. a self-closing aperture). Various types of reclosable apertures are disclosed herein including flap valves and pierceable membranes. In one embodiment, the reclosable aperture comprises a flap and an associated biasing means configured to bias the flap into a closed position.

"Radially expansible element" means a body that is expansible from a contracted delivery configuration to an expanded deployed configuration. The body may take many forms, for example a wireframe structure formed from a braided or meshed material. Examples of expandable wireframe structures suitable for transluminal delivery are known in the literature and described in, for example, WO01/87168, U.S. Pat. No. 6,652,548, US2004/219028, U.S. Pat. Nos. 6,454,775, 4,909,789, 5,573,530, WO2013/109756. Other forms of bodies suitable for use with the present invention include plate or saucer shaped scaffolds, or inflatable balloons, or stents. In one embodiment, the body is formed from a metal, for example a shape-memory metal such as nitinol. The body may have any shape suitable for the purpose of the invention, for example discoid or spheroid. In one embodiment, the body comprises a tissue ablation device. In one embodiment, the ablation device comprises an array of electrical components. In one embodiment, the array of electrical components is configured to deliver ablative energy in a specific pattern while mapping temperature. In one embodiment, the array of electrical components is configured for pacing the cardiac tissue for confirmation of ablation and disruption of chaotic signalling from the LAA. In one embodiment, a distal face of the radially expansible element comprises a covering configured to promote epithelial cell proliferation. In one embodiment, the body comprises a stepped radial force stiffness profile from distal to proximal device. In one embodiment, the body comprises a metal mesh cage scaffold. In one embodiment, a coupling between the body and the catheter member is located distally to the left atrial facing side of the body. In one embodiment, the body in a deployed configuration has a radial diameter at least 10% greater than the radial diameter of the left atrial appendage at a point of deployment. In one embodiment, the furthermost distal body is configured to be atraumatic to cardiac tissue. In one embodiment, the body covering is configured to self-close on retraction of the delivery component (i.e. catheter member). In one embodiment, the body comprises a braided mesh scaffold that in one embodiment is conducive to collagen infiltration on thermal energy delivery to promote increased anti migration resistance. In one embodiment, the array of electrodes generates an electrical map or profile of the ablation zone and the surrounding tissue electrical impedance measurements to characterise the electrical properties of the tissue, wherein the characterisation is optionally used as a measurement and confirmation of ablation effectiveness.

"Modular active element" refers to a device that is designed for detachable engagement in a recessed conduit formed in the docking station. The modular active element may be a treatment element or a sensing element, and is generally configured for removal from the docking station while it is in-situ in the heart and replaced with a different modular active element (for example replacement of a tissue ablation module with a heart parameter sensor), or replaced with a new version of the same modular active element, or the same modular active element with a new battery. The treatment or sensing element may be configured for a treatment or sensing operation applied to the LAA, the heart, a chamber of the heart (for example the left atrium), or the blood passing through the heart. The modular active element and recessed conduit (socket) are generally configured for detachable engagement to allow detachment and retraction of the modular active element, and re-attachment of the same or a different modular active element, while the docking station remains in-situ in the LAA of the heart. In one embodiment, the modular active element is dimensioned to fit within the heart. In one embodiment, the modular active element is dimensioned to fit within the left atrium (including the left atrial appendage). In one embodiment, the modular active element is dimensioned to fit within the left atrial appendage.

"Closure" or "Cover" typically means a layer disposed on the proximal side of radially expansible element covering the opening into the recessed socket. It is intended to prevent blood flow past the occlusion apparatus into the LAA. It may be formed from a woven mesh material, and may include a re-closable closure, for example an overlapping flap of material or a polymeric valve, or it may comprise a pierceable cover. In some embodiment, the connecting hub is disposed in a recess between the cover and the concave proximal face of the radially expansible body.

"Covering/cover configured to promote epithelial cell proliferation" means a material that is use promotes epithelialisation of the distal or proximal body. In one embodiment, the covering is a membrane that comprises agents that promote epithelial cell proliferation. Examples include growth factors such as fibroblast growth factor, transforming growth factor, epidermal growth factor and platelet derived growth factor, cells such as endothelial cells or endothelial progenitor cells, and biological material such as tissue or tissue components. Examples of tissue components include endothelial tissue, extracellular matrix, sub-mucosa, dura mater, pericardium, endocardium, serosa, peritoneum, and basement membrane tissue. In one embodiment, the covering is porous. In one embodiment, the covering is a biocompatible scaffold formed from biological material. In one embodiment, the covering is a porous scaffold formed from a biological material such as collagen. In one embodiment, the covering is a lyophilised scaffold.

"Radially expansible" means expansible from a contracted configuration suitable for delivery to a deployed expanded position. Typically, the bodies are radially expansible about a longitudinal axis of the device. One or both of the bodies may be self-expansible. In another embodiment, the bodies are not self-expansible, but are configured for manual deployment. Expansible bodies configured for manual expansion are described in PCT/IE2014/000005.

"Detachable engagement" means that the modular active element and conduit are configured to allow the modular active element be attached and subsequently detached from the conduit, allowing the modular active element to be detached from the conduit and withdrawn from the body and replaced with the same or a different modular active element. Various means of detachable attachment are described herein, including snap-fit, friction fit, threaded screw, and magnetic arrangements.

"Transluminal delivery" as applied to a device of the invention or part thereof (docking station or modular active element) means delivery to a target site (for example the heart) heart through a body lumen, for example delivery through an artery or vein. In one embodiment, the device of the invention is advanced through an artery or vein to deliver the occlusion apparatus to the left atrium of the heart and at least partially in the LAA.

"Anchor" as applied to the docking station, means a projection, typically on a periphery of the body, configured to project into the wall of the LAA. Examples of suitable anchors include hooks or barbs. Generally, the anchor comprises a plurality of individual anchors, for example disposed around a periphery of the radially expansible element.

"Sensor" or "sensing element" means an electrical sensor configured to detect an environmental parameter within or proximal of the LAA, for example blood flow, electrical signal activity, pressure, impedance, moisture, temperature, radiation, or the like. The sensor may include an emission sensor and a detection sensor that are suitably spaced apart. In one embodiment, the sensor is an electrode. In one embodiment, the sensor is configured to detect fluid flow. In one embodiment, the sensor is configured to detect electrical conductivity. In one embodiment, the sensor is configured to detect electrical impedance. In one embodiment, the sensor is configured to detect an acoustic (i.e. opto-acoustic and acousto-optic) signal. In one embodiment, the sensor is configured to detect an optical signal typically indicative of changes in blood flow in the surrounding tissue. In one embodiment, the sensor is configured to detect stretch. In one embodiment, the sensor is configured to detect moisture. In one embodiment, the sensor is configured for wireless transmission of a detected signal to a processor. The sensor may be employed in real time during the method of the invention to allow a surgeon determine when the LAA is sufficiently occluded, for example determining blood flow or electrical activity within the LAA. Examples suitable sensor include optical sensors, radio frequency sensors, microwave sensors, sensors based on lower frequency electromagnetic waves (i.e. from DC to RF), radiofrequency waves (from RF to MW) and microwave sensors (GHz). In one embodiment, the device of the invention is configured for axial movement of the sensor relative to the radially expansible body. In one embodiment, the device of the invention is configured for rotational movement of the sensor, typically about a longitudinal axis of the device. This helps positioning of the sensor and helps achieve full circumferential sensing. In one embodiment, the sensor is configured to detect a parameter of the left atrium. In one embodiment, the sensor is configured to perform in-vivo dosimetry to detect radiation dose, ideally in real time.

"Optical sensor" means a sensor suitable for detecting changes in blood flow in tissue, and which generally involves directing light at the tissue and measuring reflected/transmitted light. These sensors are particularly sensitive for detecting changes in blood flow in adjacent tissue, and therefore suitable for detecting devascularisation of tissue such as the LAA. Examples include optical probes using pulse oximetry, photoplasmography, near-infrared spectroscopy, Contrast enhanced ultrasonography, diffuse correlation spectroscopy (DCS), transmittance or reflectance sensors, LED RGB, laser doppler flowometry, diffuse reflectance, fluorescence/autofluorescence, Near Infrared (NIR) imaging, diffuse correlation spectroscopy, and optical coherence tomography. An example of a photopeasmography sensor is a device that passes two wavelengths of light through the tissue to a photodetector which measures the changing absorbance at each of the wavelengths, allowing it to determine the absorbances due to the pulsing arterial blood alone, excluding venous blood, muscle, fat etc). Photoplesmography measures change in volume of a tissue caused by a heartbeat which is detected by illuminating the tissue with the light from a single LED and then measuring the amount of light either reflected to a photodiode.

"Treatment element" refers to a device configured to deliver a treatment to the heart or the blood. Examples include energy delivery elements, and drug dispensing devices (for examples devices configured to release chemical or biologically active agents such as drugs, gene therapies or the like). "Energy delivering element" refers to a device configured to receive energy and direct the energy to the tissue, and ideally convert the energy to heat to heat the tissue causing collagen denaturation (tissue ablation). Tissue ablation devices are known to the skilled person, and operate on the basis of emitting thermal energy (heat or cold), microwave energy, radiofrequency energy, radiation, other types of energy suitable for ablation of tissue, or chemicals configured to ablate tissue. Tissue ablation devices are sold by ANGIODYNAMICS, including the STARBURST radiofrequency ablation systems, and ACCULIS microwave ABLATION SYSTEMS. Examples of tissue ablating chemicals include alcohol, heated saline, heated water. Typically, the liquid is heated to at least 45° C., i.e. 45-70° C. In one embodiment, the tissue ablation device comprises an array of electrodes or electrical components typically configured to deliver heat to adjacent tissue. (alcohol, heated saline, heated water). In one embodiment, one or more of the electrodes comprises at least one or two thermocouples in electrical communication with the electrode. In one embodiment, one or more of the electrodes are configured to deliver RF or microwave energy. In one embodiment, one or more of the electrodes are configured to deliver both reversible and Irreversible electroporation. In one embodiment, one or more of the electrodes are configured to deliver by means of capacitive coupling. In one embodiment, the device of the invention is configured for axial movement of the energy delivery element relative to the radially expansible body. In one embodiment, energy delivery element comprises a radially expansible body. In one embodiment, the device of the invention is configured for rotational movement of the energy delivery element, typically about a longitudinal axis of the device. This helps positioning of the energy delivering element, and helps achieve full circumferential tissue ablation. In one embodiment, the energy delivering element comprises a radioactive material suitable for radiation therapy. In one embodiment, the energy delivering element is configured to administer a radioactive material to the tissue, for example a radioactive substance such as pellets or a gel. The radioactive substance may comprise a radioactive iodine, cesium or palladium isotope. In one embodiment, the substance takes the form of "seeds," which are small (typically approximately 0.8×4.5 mm) cylinders that contain a radioactive element in a stainless-steel casing. A number of seeds, usually ranging from 80-120 seeds, are placed contact with the cardiac tissue by attaching these to the scaffold or to the radially extensibly elements. The seeds can remain in place permanently while the emitted radiation decays over time. The common radioisotopes used in the seeds are iodine-125, palladium-103 and cesium-131. Over a period of weeks or months, the level of radiation emitted by the sources will decline to almost zero. The inactive seeds then remain in the treatment site with no lasting effect. The goal of the seeds is to ensure that the total dose received by the cardiac cells is sufficient to kill them, permanently electrically isolating the tissue in contact with the seeds.

"Atrial fibrillation" or "AF" is a common cardiac rhythm disorder affecting an estimated 6 million patients in the United States alone. AF is the second leading cause of stroke in the United States and may account for nearly one-third of strokes in the elderly. In greater than 90% of cases where a blood clot (thrombus) is found in the AF patient, the clot develops in the left atrial appendage (LAA) of the heart. The irregular heart beat in AF causes blood to pool in the left atrial appendage, because clotting occurs when blood is stagnant, clots or thrombi may form in the LAA. These blood clots may dislodge from the left atrial appendage and may enter the cranial circulation causing a stroke, the coronary circulation causing a myocardial infarction, the peripheral circulation causing limb ischemia, as well as other vascular beds. The term includes all forms of atrial fibrillation, including paroxysmal (intermittent) AF and persistent and longstanding persistent AF (PLPAF).

"Ischaemic event" refers to a restriction in blood supply to a body organ or tissue, resulting in a shortage of oxygen and glucose supply to the affected organ or tissue. The term includes stroke, a blockage of blood supply to a part of the brain caused by a blood clot blocking the blood supply to the brain and the resultant damage to the affected part of the brain, and transient ischaemic events (TIA's), also known as "mini-strokes", which are similar to strokes but are transient in nature and generally do not cause lasting damage to the brain. When the restriction in blood supply occurs in the coronary arteries, the ischaemic event is known as a myocardial infarction (MI) or heart attack.

"Inductor" typically refers to a two-terminal electrical component that stores energy in a magnetic field when electric current flows through it. An inductor generally takes the form of a coil of electrical wire, with or without a magnetic core.

"Resonant power circuit" typically refers to an LC Circuit connected to a voltage or current source. The resonant power circuit generally creates a strong magnetic field that can be used to wirelessly transmit power to a receiving circuit "Desired Q factor" typically refers to the ratio between the centre frequency and bandwidth of a resonating LC circuit.

"RC circuit" typically refers to an electric circuit composed of resistors and capacitors.

"DC regulator" typically refers to an electronic component that converts non-direct current (usually alternating current) to direct current "LC circuit" typically refers to an electric circuit composed of inductors and capacitors.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Figure 1B:
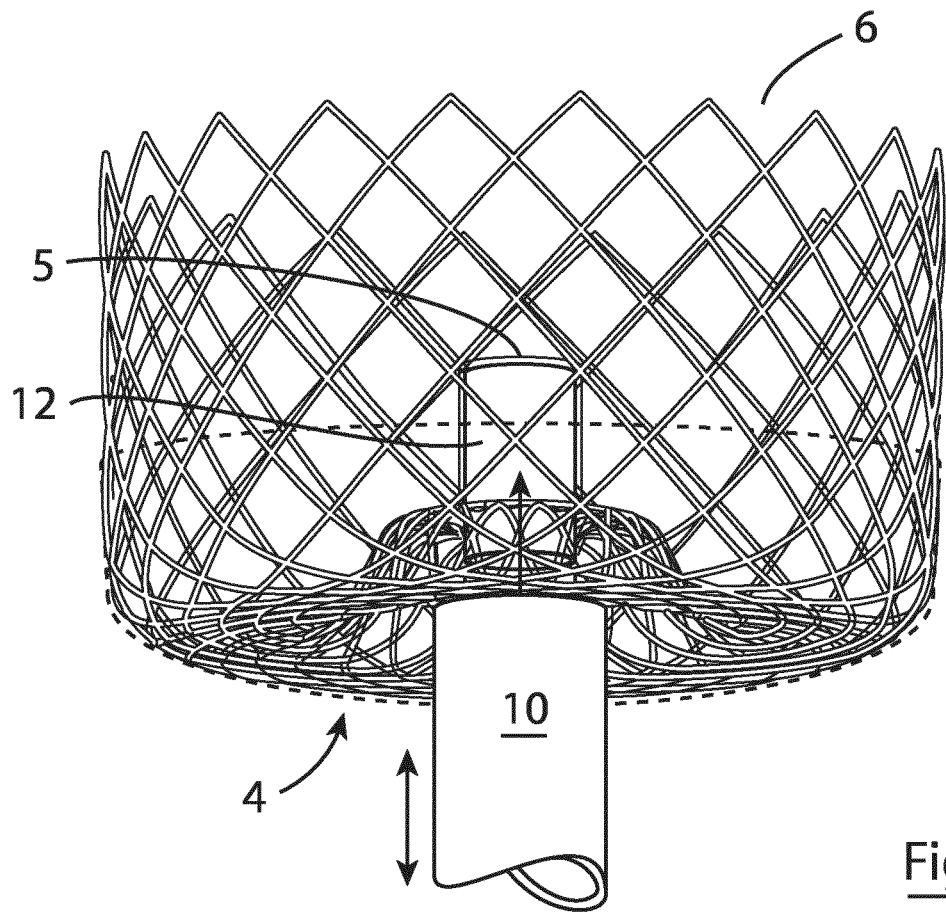
Figure 1C:
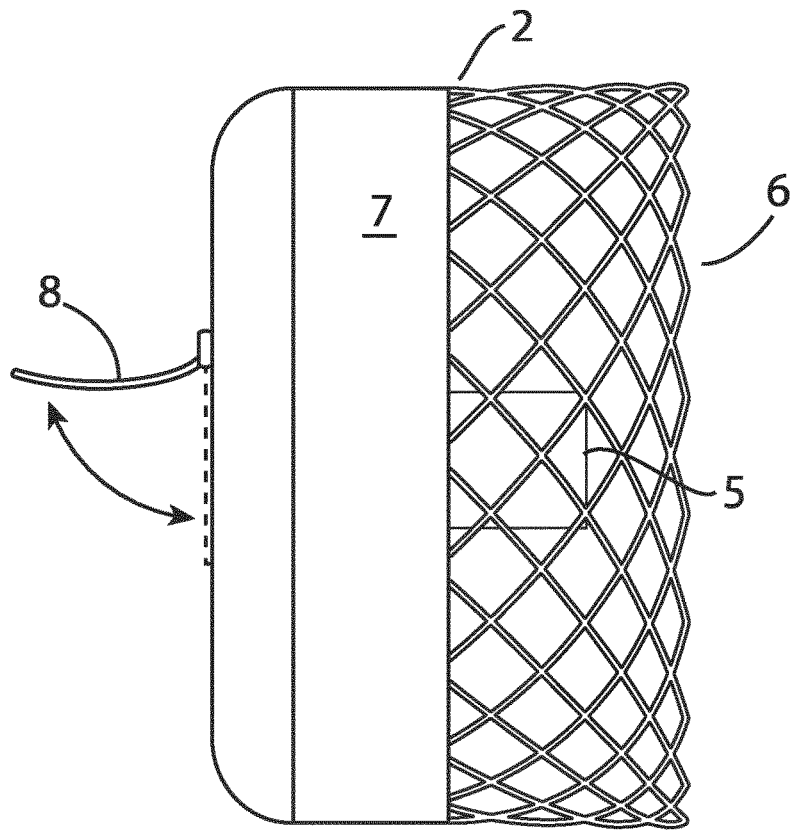
Figure 1D:
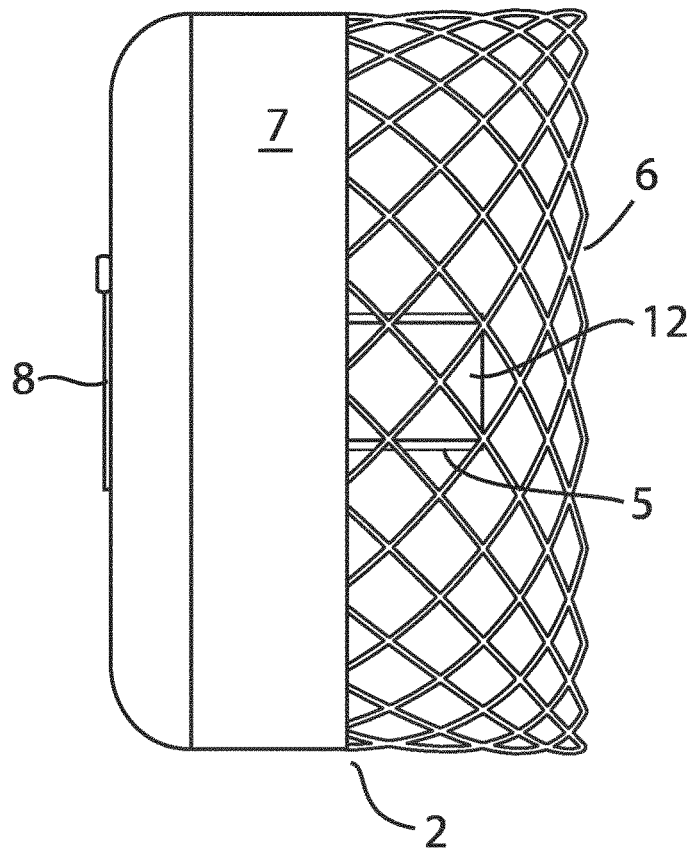
Figure 1E:
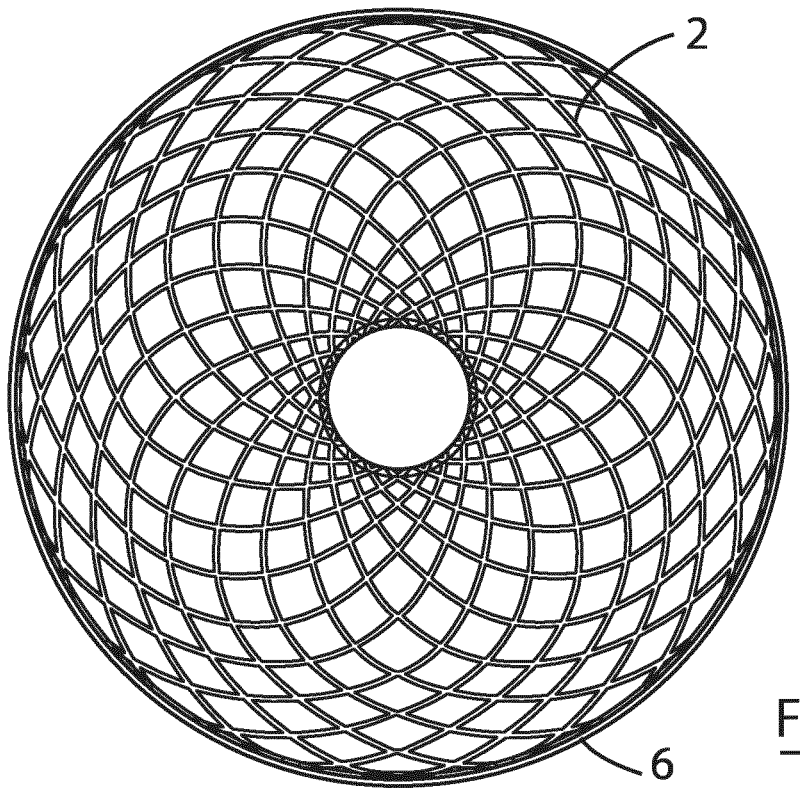
Figure 1F:
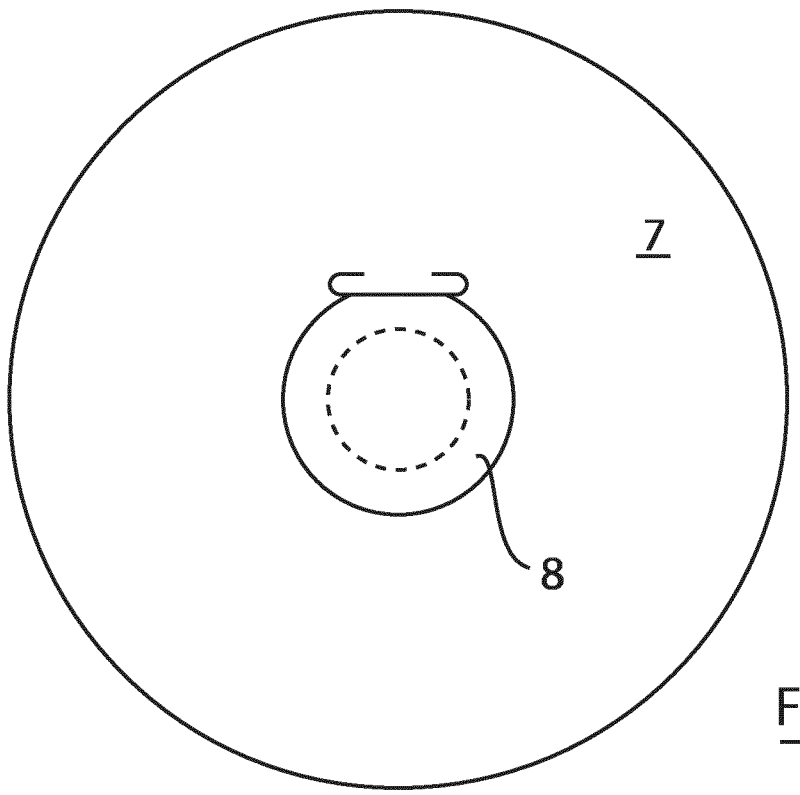

Referring to the drawings, and initially to FIGS. 1A to 1F, there is illustrated a docking station 2 forming part of the device 1 of the invention and shown in its deployed configuration, and comprising a radially expansible element (in this case, a cage 3) having a toroidal proximal end 4 (FIG. 1D) with a recessed socket 5 and cylindrical distal end 6. As shown in FIGS. 1A to 1C, the proximal end of the cage comprises a mesh cover 7 that is impermeable to blood and in use fluidically isolated the LAA from the left atrium when the device is anchored in the LAA. A re-closable aperture is provided over the recessed socket 5 in the form of a flap 8 and associated hinged spring clip 9 configured to bias the flap into a closed position. The purpose of the re-closable aperture is to allow access to the recessed socket from the left atrium when the modular active element is being removed and replaced, and at other times fluidically isolate the recessed socket from the left atrium. In FIG. 1B, a modular active element 12 is shown engaged within the recessed socket 5, and a delivery catheter 10 is shown abutting a mouth of the recessed socket 5.

FIGS. 2A and 2B illustrate one embodiment of a re-closable flap 8 formed on the mesh cover 7 comprising a plurality of valve leaflets 11 that are biased into a closed orientation shown in FIG. 2A and can be pushed inwardly upon application of a force to an open configuration shown in FIG. 2B. The valve material employed in the leaflets can be the same material employed in replacement heart valves like the TAVI, for example porcine epicardium tissue.

FIGS. 2C to 2F illustrate the operation of the valve. In FIG. 2C it is shown in a closed configuration, fluidically isolating the left atrium from the LAA and the recessed socket 5. In FIG. 2D, a delivery catheter 10 containing a modular active element 12 is shown projecting through the valve, where the valve leaflets conform closely to the catheter sidewall. In FIG. 2E, the modular active element 12 has been delivered into and engaged with the recessed socket 5, and in FIG. 2F the catheter 10 has been withdrawn allowing the valve to close.

Figure 3D:
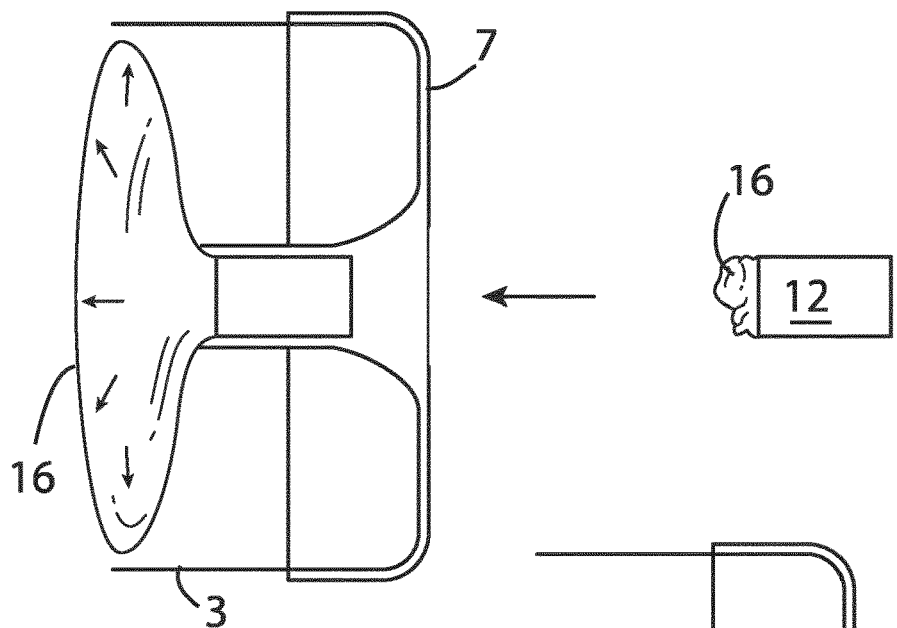
FIG. 3 shows four different ways in which the modular active element and conduit interact, namely threaded engagement (FIG. 3A), interference fit (FIG. 3B), anchor deployment (FIG. 3C), balloon deployment (FIG. 3D) and spring engagement (FIGS. 3E and 3F FIG. 4 illustrates how the modular active element can electrically connect with the tissue of the LAA through the radially expansible member.
Figure 3E:
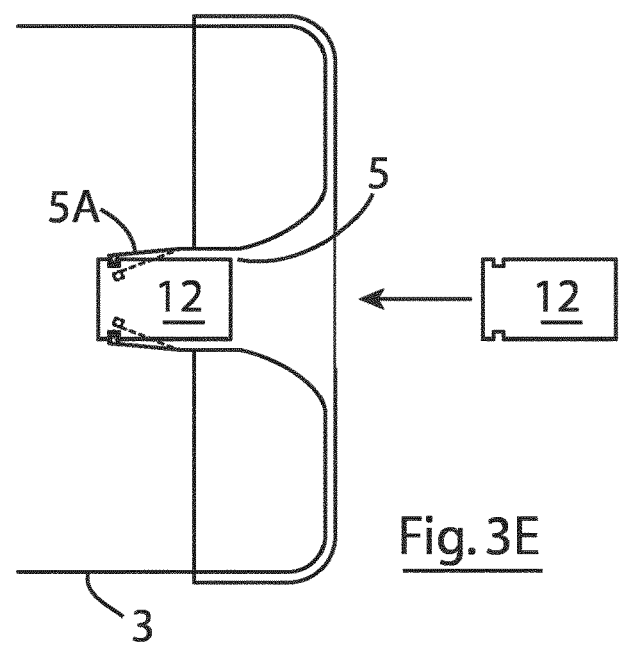
Figure 3F:
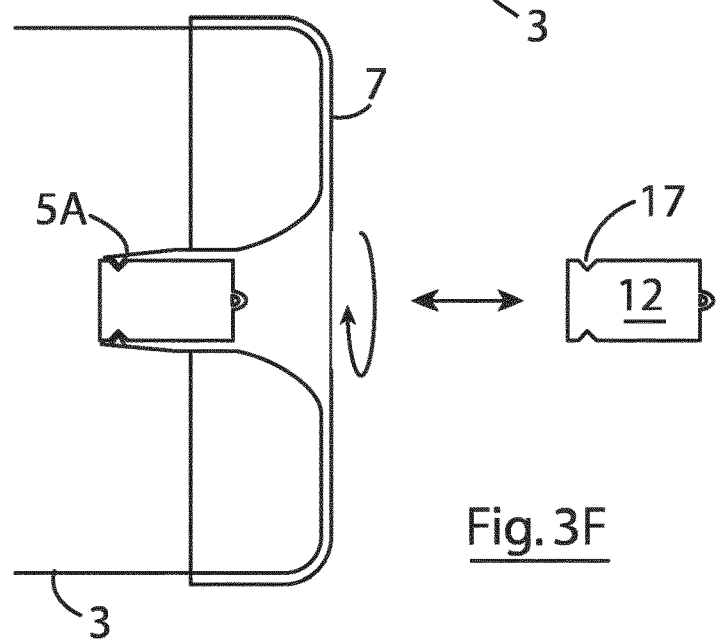

FIG. 3A—illustrate a number of different ways in which the modular active element 12 and recessed socket 12 detachably engage, namely: threaded engagement (FIG. 3A) in which a modular active element 12 and internal wall of the recessed socket 5 have cooperating threads configured to allow the modular active element 12 screw into the recessed socket; interference fit (FIG. 3B) in which the element 12 has a distal end 12A configured for radial expansion to friction fit in the conduit; anchor deployment (FIG. 3C) in which distal and proximal ends 12A and 12B of the element 12 have anchor elements 14 configured to splay radially outwardly at each end of the conduit 5 to provide engagement, balloon deployment (FIG. 3D) in which the distal end 12A of the element 12 has an inflatable balloon 16; and spring engagement (FIGS. 3E and 3F) in which a distal end 5A of the recessed conduit 5 tapers inwardly and the distal end of the modular active element has a circumferential slot 17 dimensioned to engage the inwardly tapered end 5A of the recessed conduit.

Figure 4A:
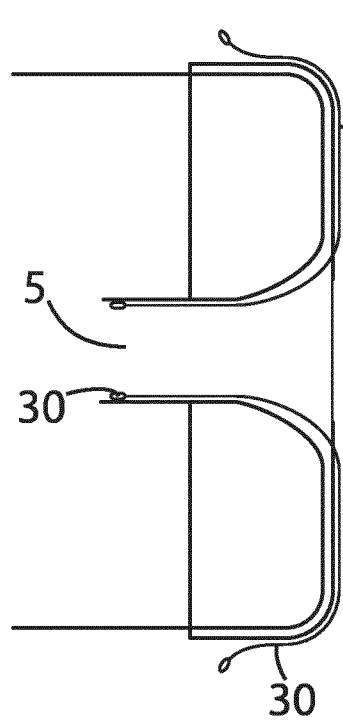
Figure 4B:
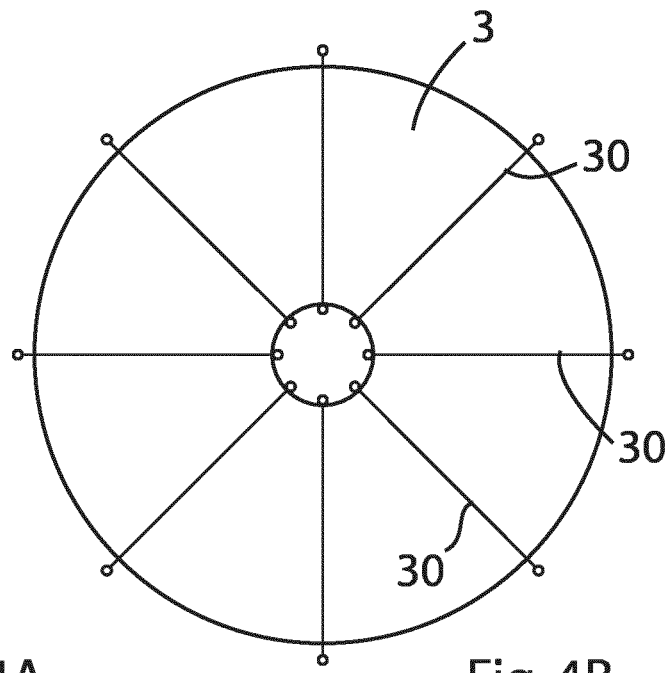
Figure 4C:
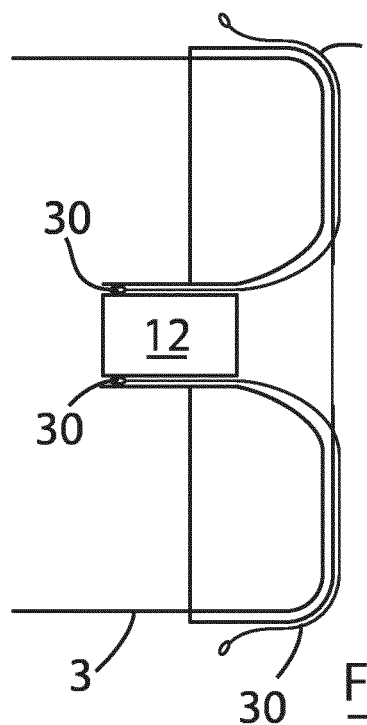

FIGS. 4A, 4B and 4C illustrate an embodiment of the device of the invention in which the radially expansible element 3 comprises a series of radial electrically conducting elements 30 providing electrical communication between the modular active element 12 when it is engaged in the recessed socket 5 and the wall of the LAA. In this embodiment, the conducting elements are attached to an inside of the mesh cover, and may be used as an energy delivery element to deliver ablative energy from the modular active element 12 to the wall of the LAA to electrically isolate the LAA. In another embodiment, the conductive elements 30 may be sensors configured to detect a parameter of the wall of the LAA.

Figure 5:
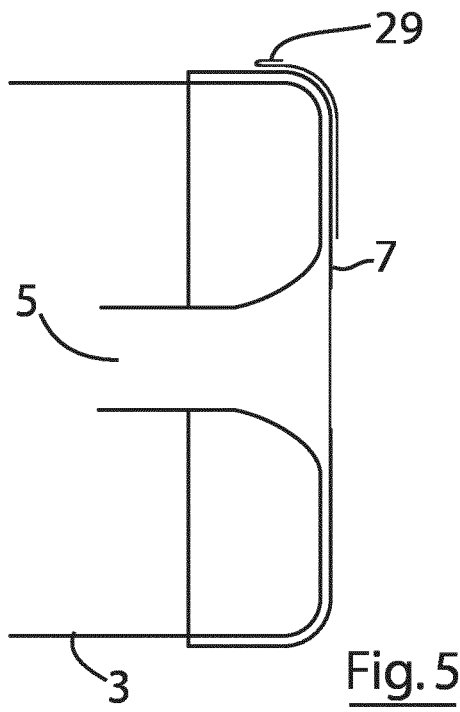
FIG. 5 illustrates how the proximal end of the radially expansible element can have a sealing skirt configured to engage irregular shaped LAA's

FIG. 5 illustrates an embodiment of the radially expansible element where a circumferential periphery of the cage 3 has a double layer of mesh 29 configured to more easily circumferentially engage a wall of the LAA, and may include bristles, or be frayed, or incorporate one-way anchors.

Figure 6A:
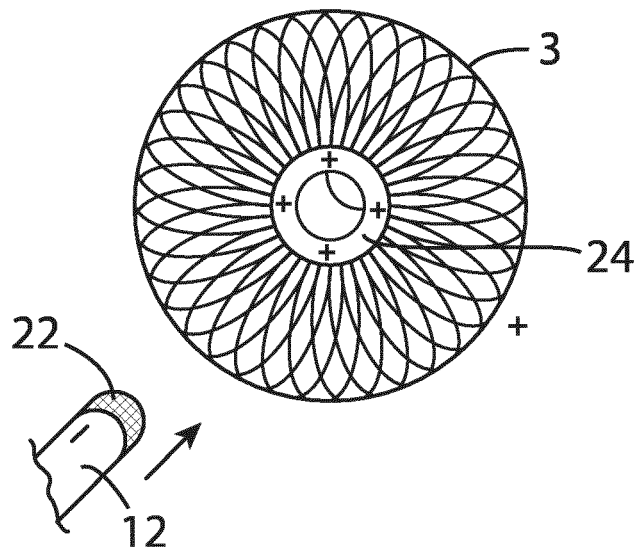
FIGS. 6A, 6B and 6C illustrate a delivery catheter for the modular active element incorporating a magnet to help guide the delivery catheter towards the opening of the conduit.
Figure 6B:
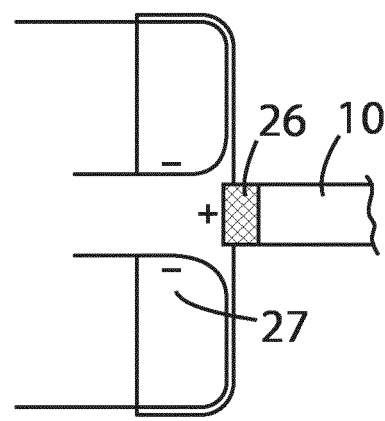
Figure 6C:
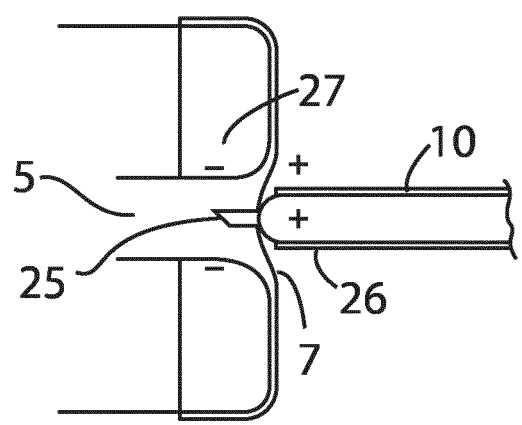

FIG. 6A illustrates an embodiment of the device of the invention in which the distal end of the modular active element 12 incorporates a magnet of a first polarity 22 and the periphery of the recessed socket 5 incorporates a magnet of second polarity 24 to facilitate insertion of the element 12 into the recessed socket 5. FIG. 6B illustrates another embodiment of the device of the invention in which a delivery catheter 10 has a magnetised head of first polarity 26 and the periphery of the recessed socket 5 incorporates a magnet of second polarity 27 to docking the catheter and the recessed socket during delivery of the modular active element 12. FIG. 6C illustrates another embodiment of the device of the invention in which a delivery catheter 10 has a magnetised head of first polarity 26 and the periphery of the recessed socket 5 incorporates a magnet of second polarity 27 to docking the catheter and the recessed socket during delivery of the modular active element 12. In this embodiment, the modular active element 12 is disposed within the catheter 10 has a piercing tip configured to pierce the mesh cover 7.

Figure 7A:
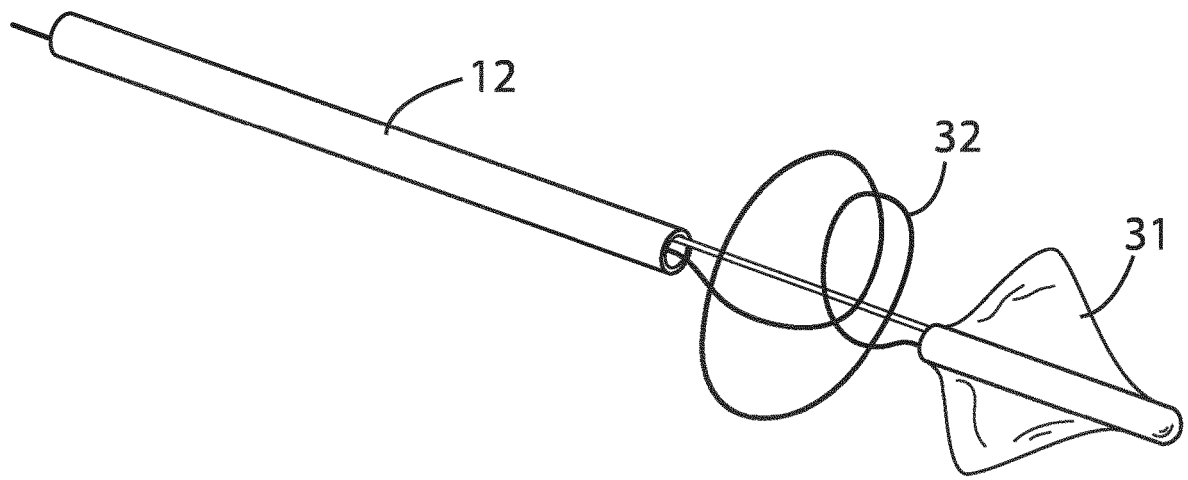
FIG. 7A shows the modular active element in a deployed active configuration.
Figure 7B:
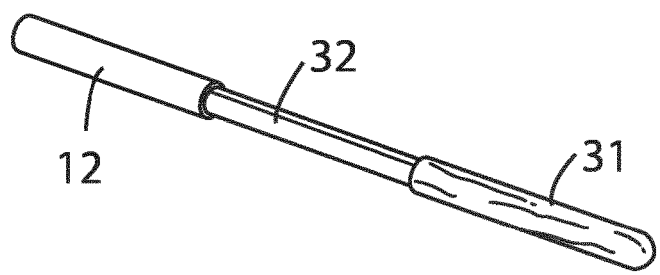
FIG. 7B shows the modular active element in a retracted delivery configuration.
Figure 7C:
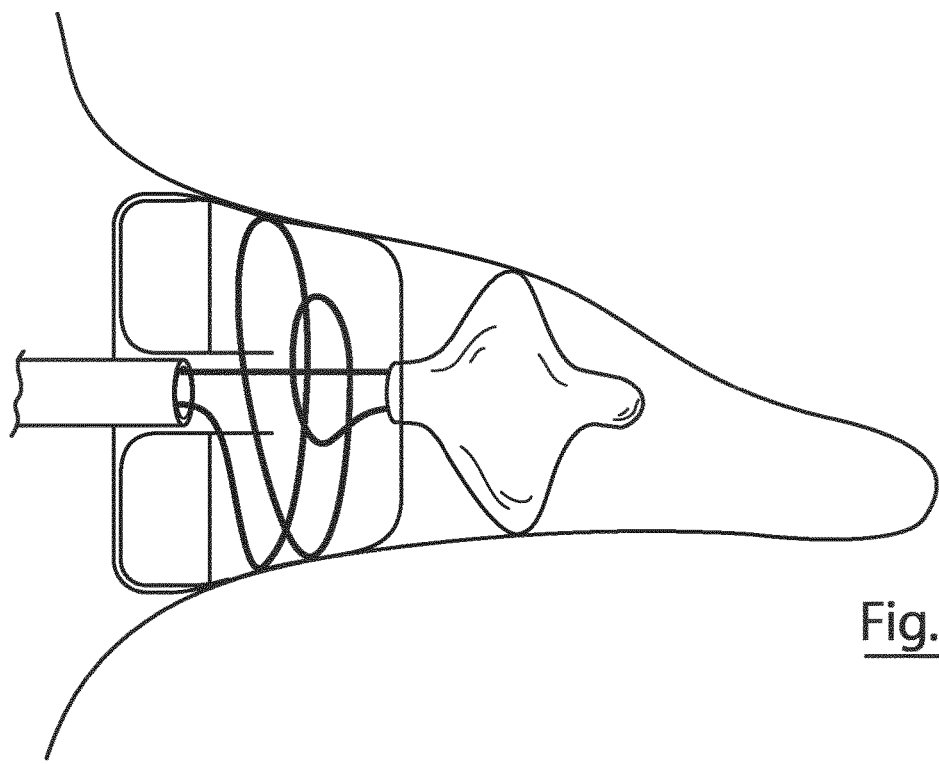
FIG. 7C shows the deployed modular active element engaged within the conduit.

FIG. 7 illustrates a tissue ablation modular active element forming part of a device of the invention, and having an inflatable balloon 31, and a radially expandable RF electrode coil 32 disposed distally of the RF electrode: In this embodiment, the device of the invention comprises a catheter 10 that remains attached to the modular active element 12 during use of the device. The catheter and modular active element are configured to be withdrawn from the docking station and transluminally withdrawn from the patient. The modular active element may be detached from the catheter, and replaced with another modular active element before being transluminal delivered to the left atrium and re-engaged with the docking station through the recessed socket and deployed. FIG. 7A shows the modular active element in a partially deployed active configuration, and FIG. 7B shows the modular active element in a retracted delivery configuration. FIG. 7C shows the deployed modular active element deployed and anchored in the LAA, with a RF coil 32 deployed within the cage 12 and in contact with the LAA tissue for tissue ablation.

Figure 8A:
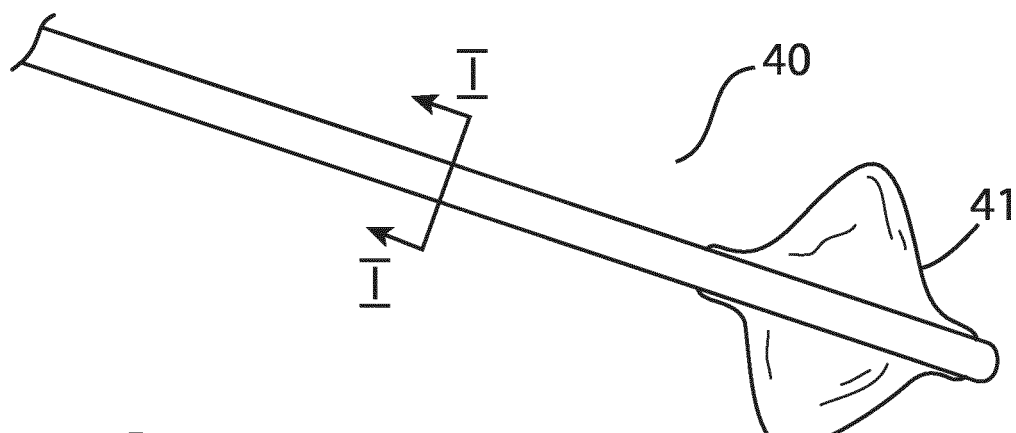
FIG. 8A shows a modular active element comprising an inflatable balloon.
Figure 8B:
FIG. 8B is a sectional view taken along the lines H of FIG. 8A.
Figure 8C:
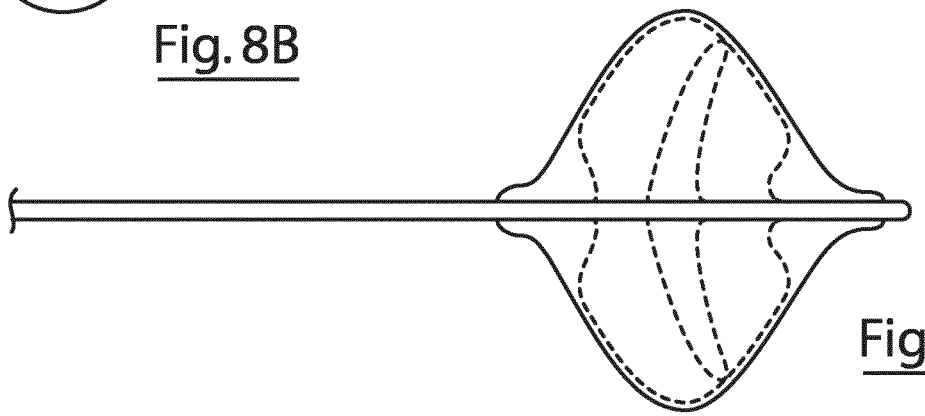
FIG. 8C shows a modular active element comprising an inflatable balloon having different compartments configured to deliver different cryogenic ablation treatments.

FIG. 8A shows a modular active element 40 comprising a coaxially mounted inflatable balloon 41, FIG. 8B is a sectional view taken along the lines I-I in FIG. 8A illustrating a number of separate lumens in the element 40, for inflation and deflation of the balloon, for providing light and for optical imaging. FIG. 8C shows a modular active element comprising an inflatable balloon having different compartments configured to deliver different cryogenic ablation treatments. The ablation treatment can be zonally controlled or activated depending on ablation application (i.e. distal zone and proximal facing zone).

Figure 9:
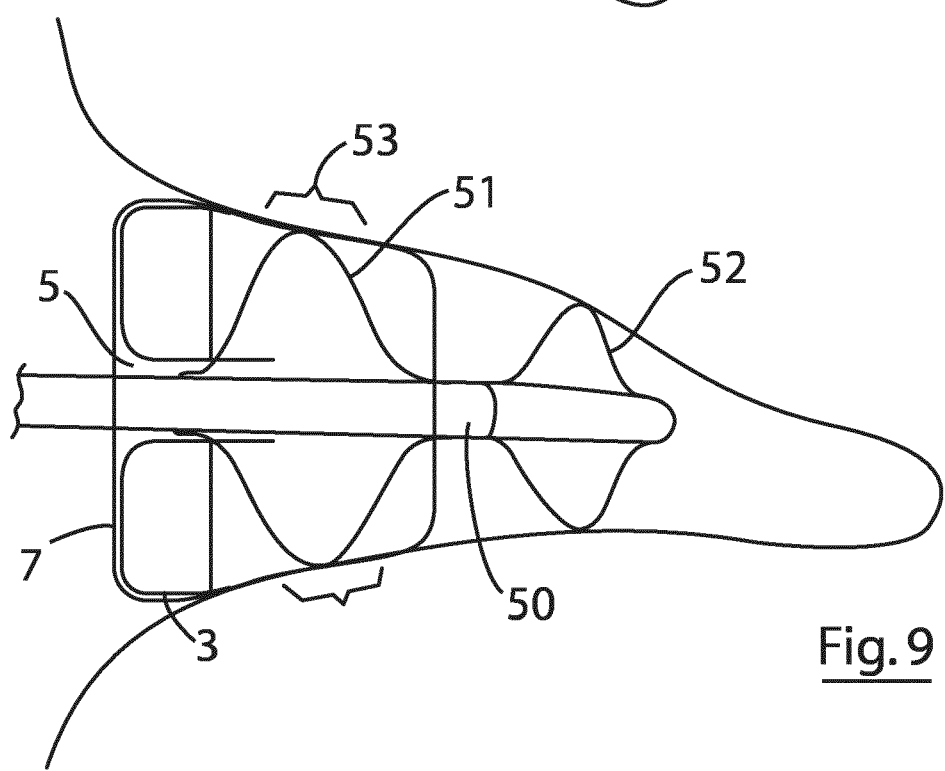
FIG. 9 shows a modular active element having two inflatable balloons engaged within the conduit.

FIG. 9 shows a modular active element 50 having two inflatable balloons 51, 52 engaged within the LAA. In the embodiment, the first balloon 51 may be configured to deliver a cryogenic treatment to the adjacent LAA tissue, to ablate the tissue at treatment area 53, and the second balloon 52 may be configured to receive a warm fluid to heat the tissue in the vicinity of the phrenic nerve to protect the nerve from ablation due to the cryogenic treatment in the adjacent treatment area 53.

Figure 10:
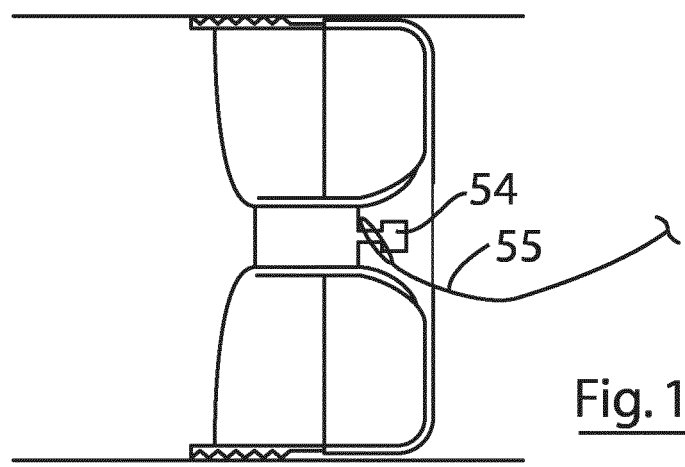
FIG. 10 illustrates a modular active element incorporating a hook configured for engagement with a delivery/removal device.

FIG. 10 shows an embodiment of a modular active element forming part of a device of the invention in which a proximal end of the element 12 comprises an extension 54 that can be gripped with a snare 55 to enable removal of the modular active element 12 from the recessed socket 5.

Figure 11A:
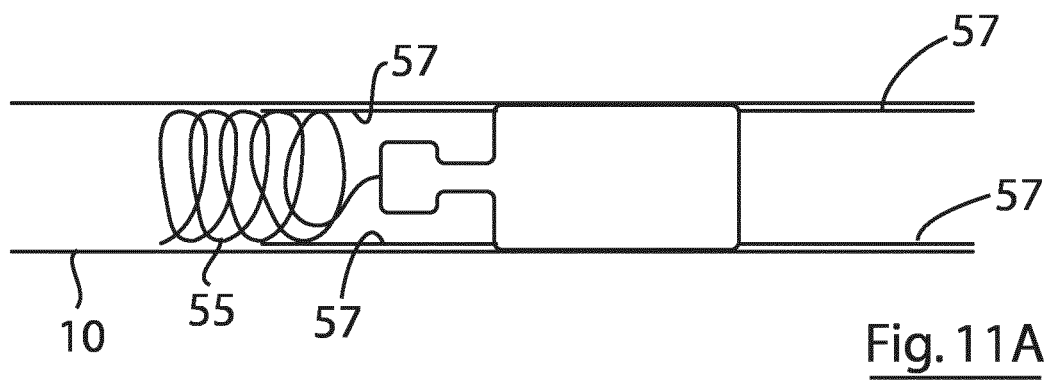
FIGS. 11A and 11B illustrate a device for left atrial monitoring incorporating an induction coil for remote powering or charging of the device.
Figure 11B:
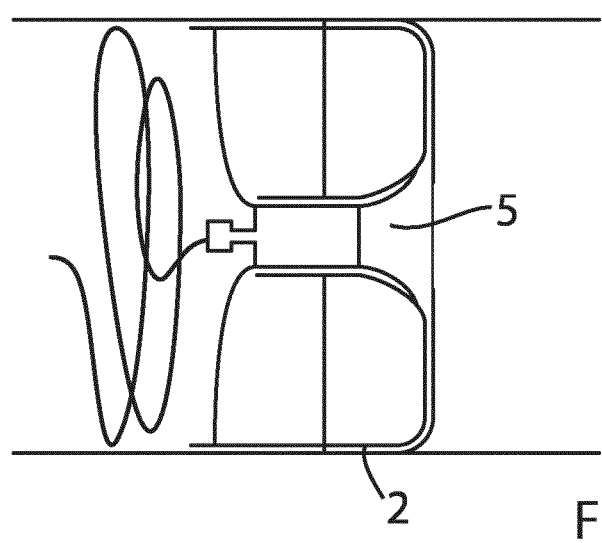

FIG. 11 shows an embodiment of a modular active element forming part of a device of the invention in a delivery configuration (FIG. 11A) inside a delivery catheter 10, and a deployed configuration (FIG. 11B) engaged within a recessed socket 5 of a docking station 2. The modular active element comprises a charging coil 55 operably connected to a battery 56, and having distal and proximal anchoring arms 57 biased to splay outwardly when the element is ejected from the delivery catheter and anchor the element within the recessed socket. The coil 55 is configured to receive power from an external source and relay data to a remote receiver.

Figure 12A:
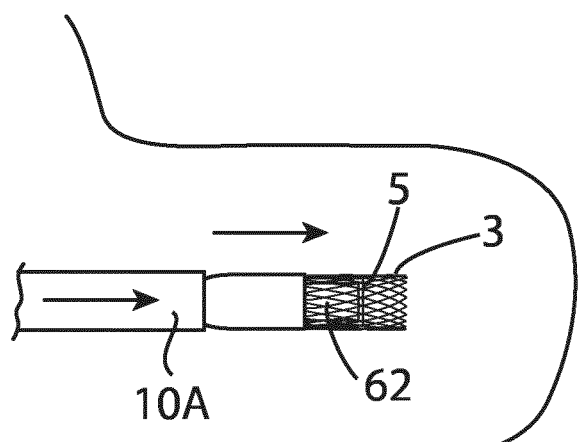
FIGS. 12A to 12H illustrates a method of using the device of the invention.
Figure 12B:
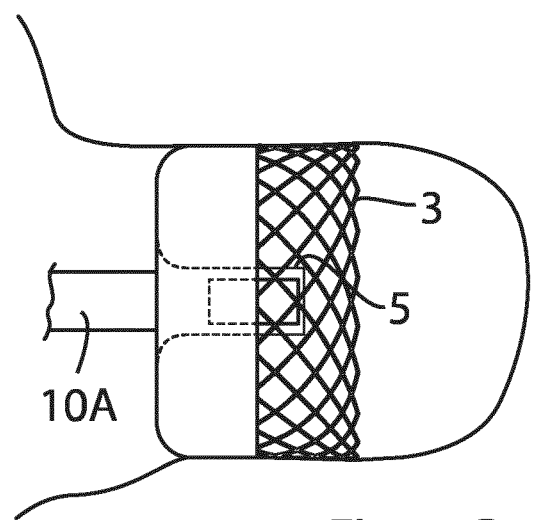
Figure 12C:
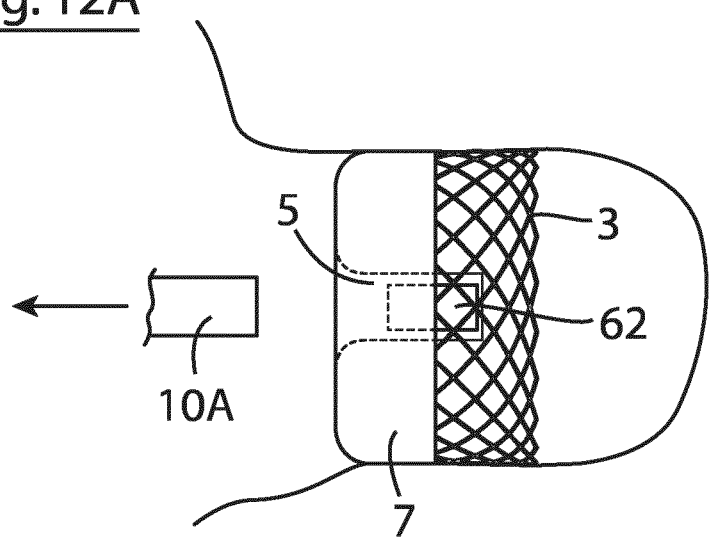
Figure 12D:
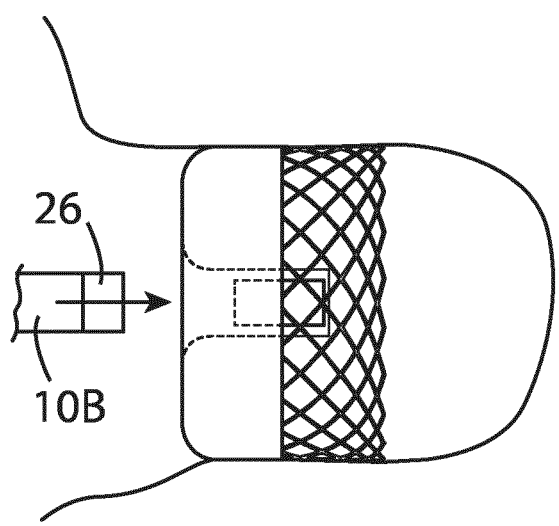
Figure 12E:
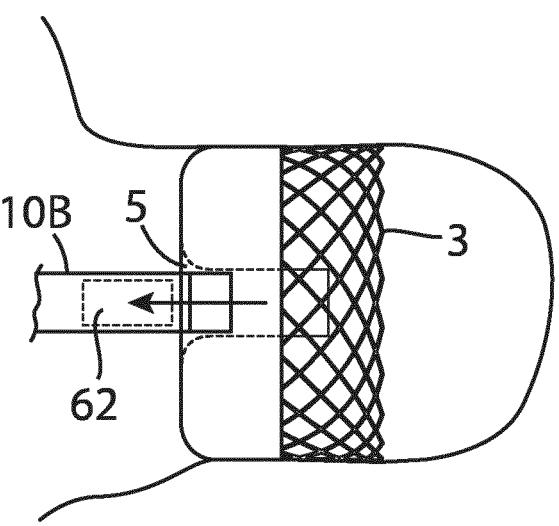
Figure 12F:
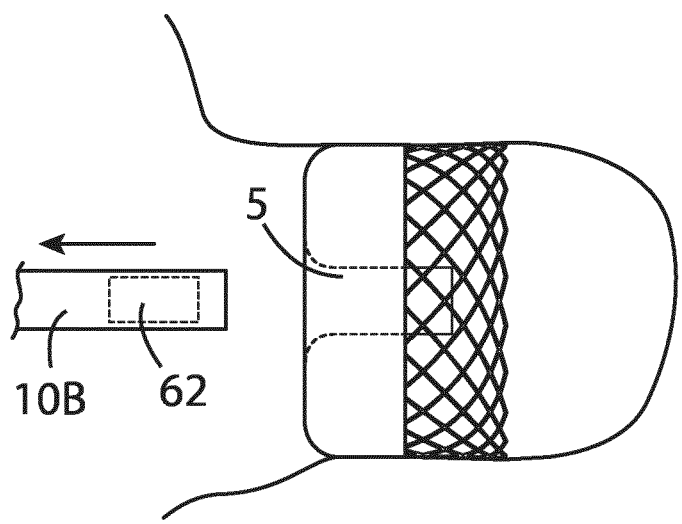
Figure 12G:
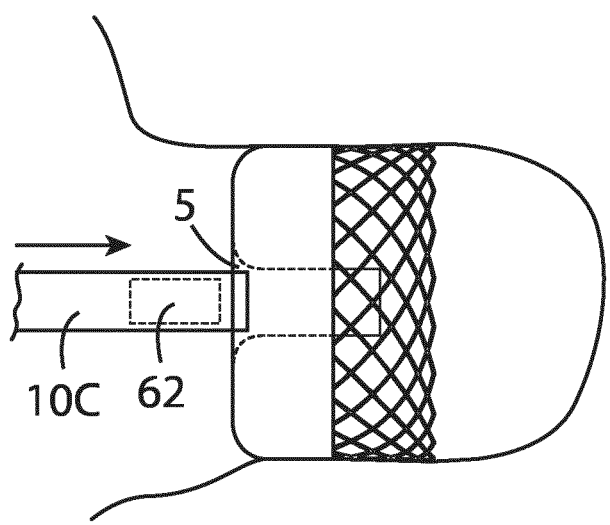
Figure 12H:
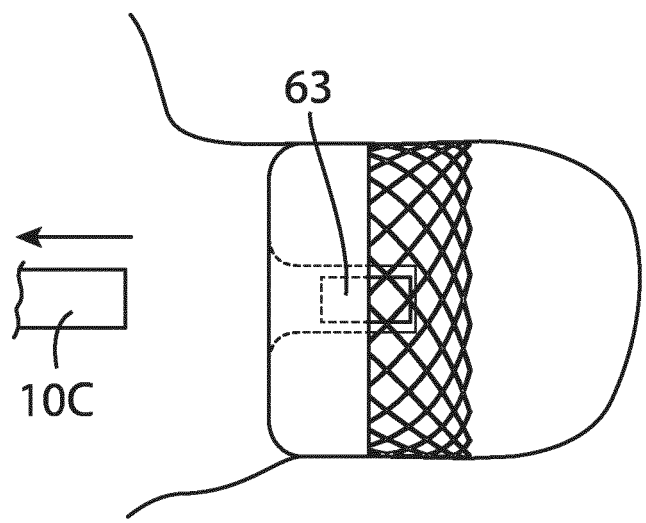

FIGS. 12A to 12H illustrated one embodiment of a method of use of the device of the invention. FIG. 1 illustrates a device of the invention attached to a delivery catheter 10A approaching the LAA of the left atrium of a human heart. FIG. 12B shows the device in a deployed configuration, with the docking station 2 anchored in the mouth of the LAA and a modular active element 62 engaged within the recessed socket 5 of the docking station. FIG. 12C shows the catheter 10A detached from the docking station prior to transluminal retraction from the heart. FIG. 12D shows a withdrawal catheter 10B having a magnetized head 26 approaching the proximal face of the docking station, and FIG. 12E shows the catheter engaged with the docking station and projecting through the re-closable valve in the cover, and the modular active element 62 retracted from the recessed socket of the docking station into the withdrawal catheter. FIG. 12F shows the withdrawal catheter 10B, with the modular active element in-situ, being transluminal withdrawn from the heart. FIG. 12G shows a replacement catheter 10C containing a replacement modular active element 63 approaching the docking station and projecting through the re-closable valve prior to delivery of the element 63 into the empty recessed socket 5 as shown in FIG. 12H.

Figure 13:
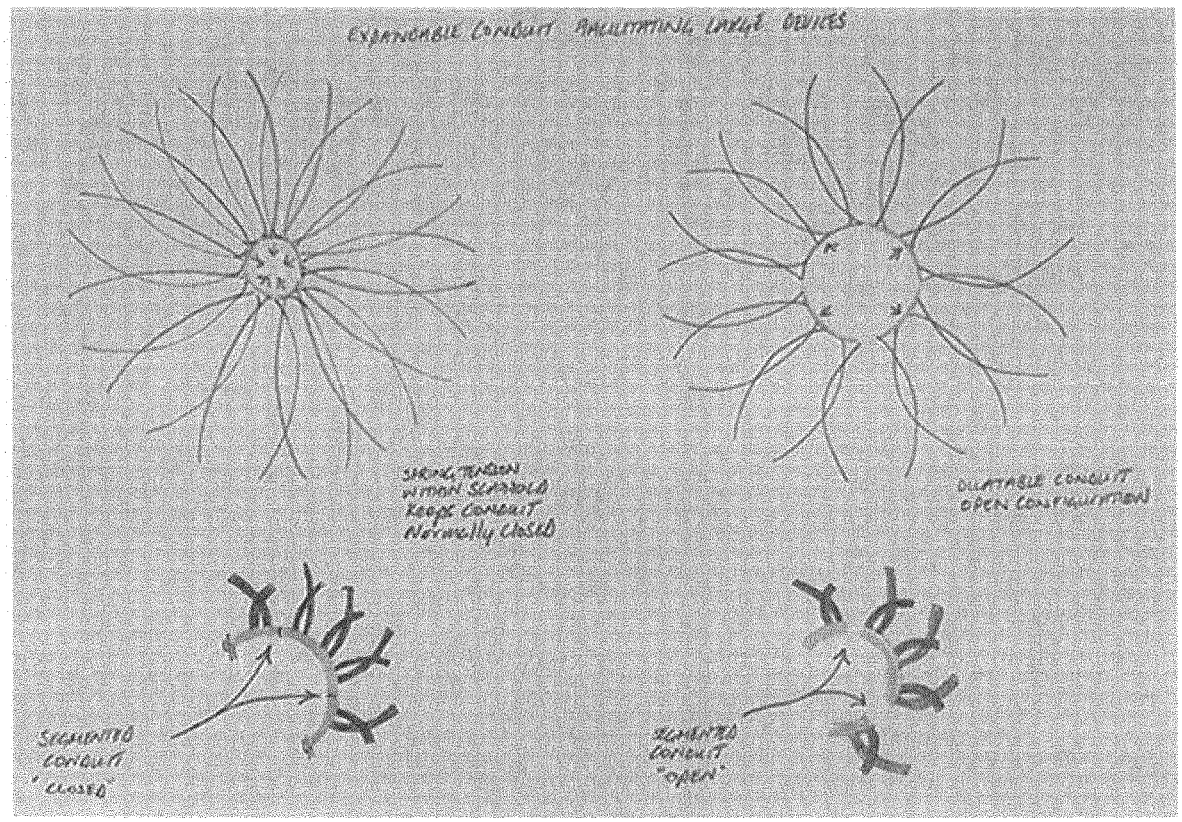
FIG. 13 is an illustration of a docking station forming part of a device of the invention having a radially expansible cage and recessed conduit (the mouth of the conduit is shown) and showing the recessed conduit in a resting configuration (left) and in an expanded configuration (right). The figures also show how the conduit may comprise longitudinal sections or segments which abut but are not connected and allow the radial expansion of the conduit.

FIG. 13 is an illustration of a docking station forming part of a device of the invention having a radially expansible cage and recessed socket (the mouth of the socket is shown) and showing the recessed socket in a resting configuration (left) and in an expanded configuration (right). The figures also show how the socket may comprise longitudinal sections or segments which abut but are not connected, and allow the radial expansion of the socket when, for example, an oversized modular active element is advanced into the socket.

Figure 14:
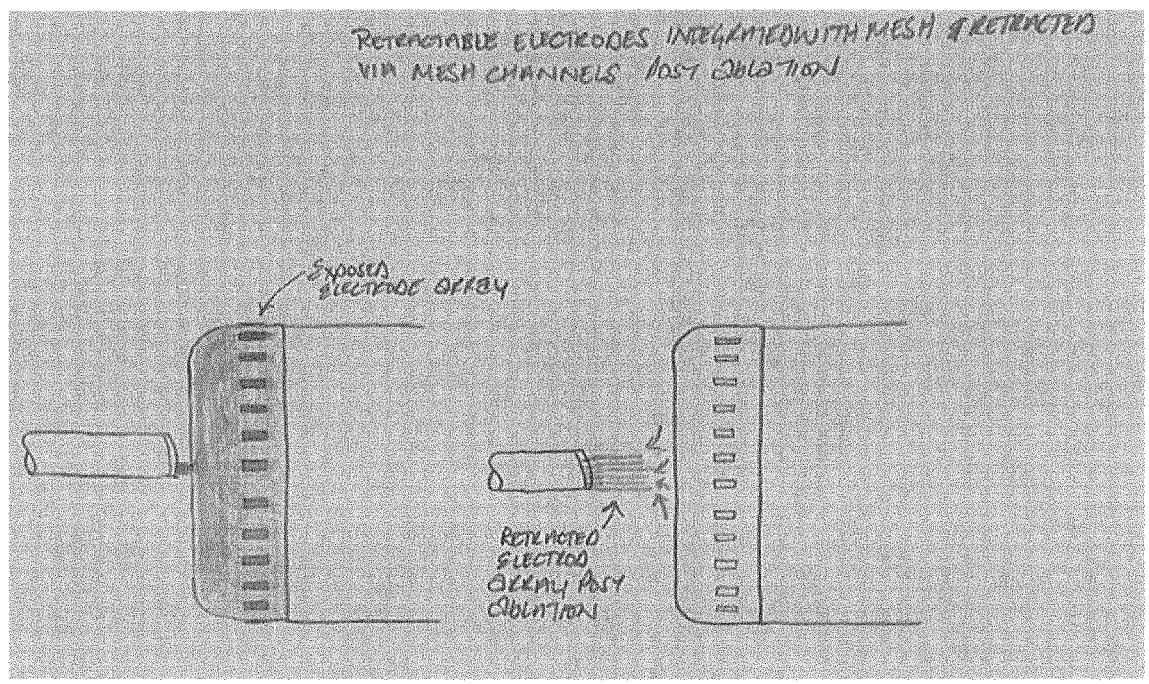
FIG. 14 shows a docking station forming part of a device according to the invention having a cover comprising a network of radial conduits configured to receive electrodes or wires and direct the wires radially outwardly to a periphery of the cover. The cover includes a circumferential arrangement of apertures configured to expose the distal end of the electrodes to the tissue when the docking station is employed in the body lumen.

FIG. 14 shows a docking station forming part of a device according to the invention having a cover comprising a network of radial conduits which are disposed on an inside face of the cover and are configured to receive electrodes or wires provided at a distal end of an associated catheter and direct the wires radially outwardly to a periphery of the cover. The cover includes a circumferential arrangement of apertures configured to expose the distal end of the electrodes to the tissue when the docking station is deployed in the body lumen.

Figure 15A:
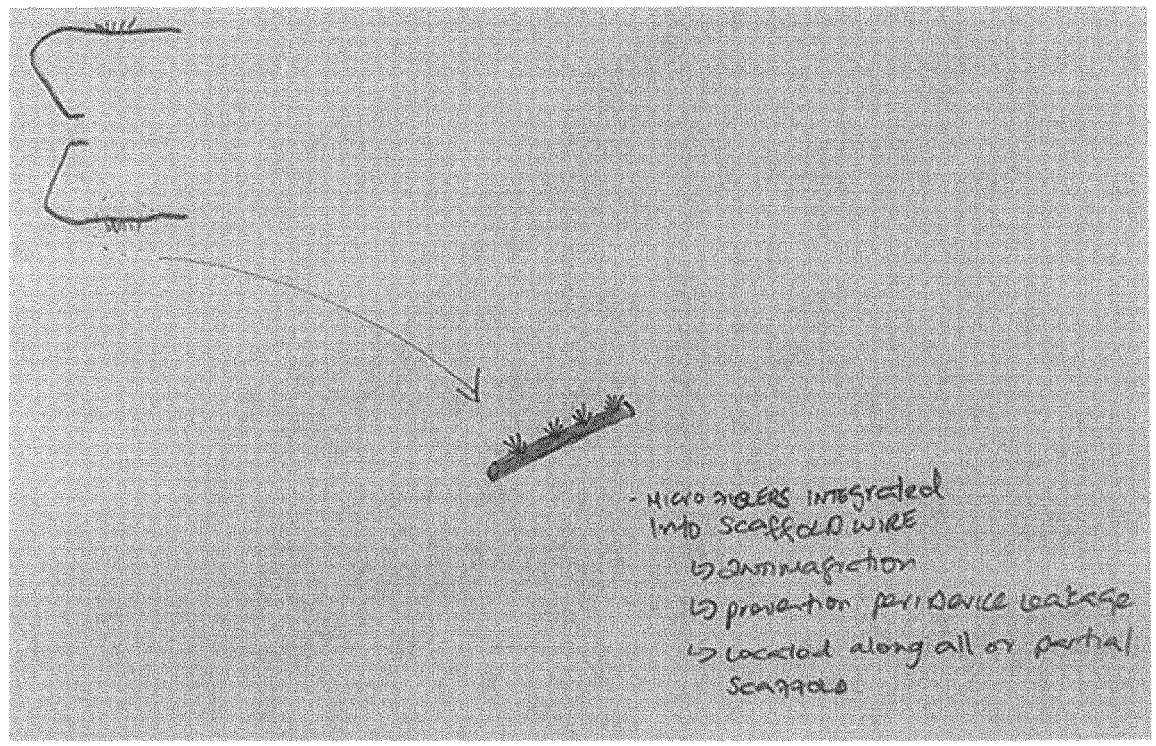
FIGS. 15A and 15B show an embodiment of the device of the invention in which the radially expansible element is a cage comprising circumferential brush members.
Figure 15B:
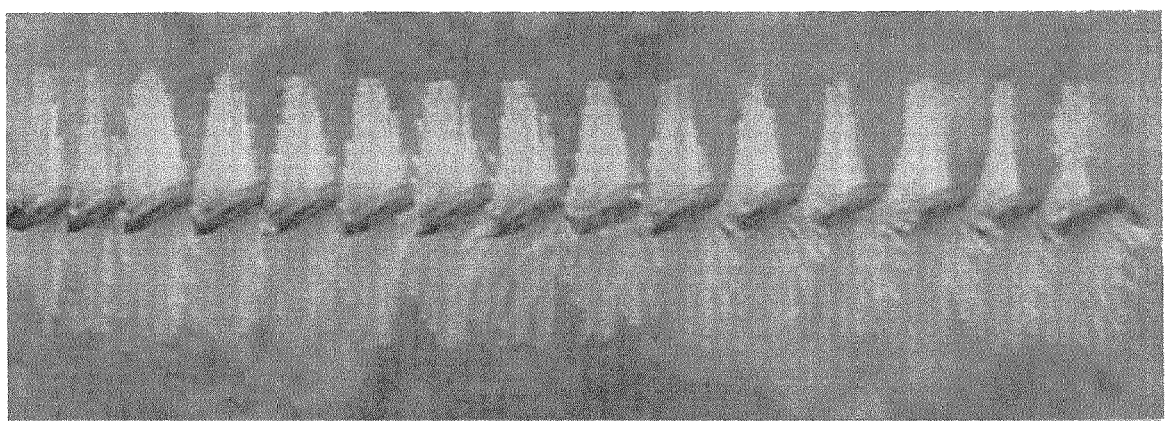

FIGS. 15A and 15B show an embodiment of the device of the invention in which the radially expansible element is a cage comprising circumferential brush members. The cage may be formed from wires, for example stainless steel or nitinol wires, and some of the wires may comprise brush members having a central spine and an arrangement of bristles extending radially outwardly of the spine.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A system comprising:
(a) a device for implantation in a left atrial appendage of a heart, comprising a docking station comprising:
a radially expansible element that is adjustable between a contracted orientation suitable for transluminal delivery and a deployed orientation configured to anchor within the left atrial appendage and fluidically isolate the left atrial appendage (LAA) from a left atrium; and
a recessed socket accessible from the left atrium through an opening, and a closure covering the opening;
(b) a modular active element configured for implantation and detachable engagement within the recessed socket of the docking station; and
(c) a delivery catheter to transluminally deliver the modular active element to the recessed socket of the docking station,
wherein the docking station comprises a tissue ablation device to deliver tissue ablative energy from the modular active element to a wall of the LAA, wherein the tissue ablation device is associated with the radially expansible element and comprises an array of electrodes and electrically conducting elements configured to provide electrical communication between the modular active element when it is engaged within the recessed socket and the wall of the LAA when the radially expansible element is deployed within the LAA.

2. The system according to claim 1, in which the modular active element is dimensioned to fit fully within the LAA.

3. The system according to claim 1, in which the modular active element is dimensioned to engage within the recessed socket to close the recessed socket.

4. The system according to claim 1, in which the closure for the recessed socket comprises a mesh cover to fluidically isolate the left atrium from the LAA when the device is deployed in the LAA, in which the mesh cover optionally comprises a self-closing aperture.

5. The system according to claim 1, in which the closure is configured to promote epithelial cell proliferation.

6. The system according to claim 1, in which the radially expansible element is a radially expansible cage.

7. The system according to claim 1, in which the radially expansible element comprises proximal part having a substantially toroidal shape and comprising an opening of the recessed socket, a cover for the recessed socket, and a distal part that is substantially cylindrical.

8. The system according to claim 1, in which the modular active element and recessed socket are configured for inter-engagement when the modular active element is fully received in the recessed socket.

9. The system according to claim 1, in which the modular active element and recessed socket are configured for screw-fit detachable engagement or interference-fit detachable engagement.

10. A system comprising:
(a) a device for implantation in a left atrial appendage of a heart, comprising:
a docking station comprising a radially expansible element that is adjustable between a contracted orientation suitable for transluminal delivery and a deployed orientation configured to anchor within the left atrial appendage and fluidically isolate the left atrial appendage from a left atrium, a recessed socket accessible from the left atrium through an opening, and a closure covering the opening; and
a modular active element configured for implantation and detachable engagement within the recessed socket of the docking station, and
(b) a delivery catheter to transluminally deliver the modular active element to the recessed socket of the docking station, in which the modular active element is configured for detachable coupling to the delivery catheter,
in which the modular active element comprises an inductor comprising an inductor coil that is adjustable between a contracted orientation suitable for transluminal delivery and a deployed radially expanded orientation.

11. A system comprising:
(a) device for implantation in a left atrial appendage of a heart, comprising:
a docking station comprising a radially expansible element that is adjustable between a contracted orientation suitable for transluminal delivery and a deployed orientation configured to anchor within the left atrial appendage and fluidically isolate the left atrial appendage from a left atrium, a recessed socket accessible from the left atrium through an opening, and a closure covering the opening; and
a modular active element configured for implantation and detachable engagement within the recessed socket of the docking station, and
(b) a delivery catheter to transluminally deliver the modular active element to the recessed socket of the docking station, in which the modular active element is configured for detachable coupling to the delivery catheter,
in which the modular active element comprises an inductor comprising an inductor coil, in which the inductor coil is disposed on a distal end of the modular active element and configured for deployment distally of a recessed conduit.

12. A system comprising:
(a) device for implantation in a left atrial appendage of a heart, comprising:
a docking station comprising a radially expansible element that is adjustable between a contracted orientation suitable for transluminal delivery and a deployed orientation configured to anchor within the left atrial appendage and fluidically isolate the left atrial appendage from a left atrium, a recessed socket accessible from the left atrium through an opening, and a closure covering the opening; and
a modular active element configured for implantation and detachable engagement within the recessed socket of the docking station, and
(b) a delivery catheter to transluminally deliver the modular active element to the recessed socket of the docking station, in which the modular active element is configured for detachable coupling to the delivery catheter,
in which the modular active element comprises a resonant power circuit configured with a plurality of coils adapted to provide a desired Q factor greater than or equal to 0.5.

13. A system comprising:
(a) device for implantation in a left atrial appendage of a heart, comprising:
 a docking station comprising a radially expansible element that is adjustable between a contracted orientation suitable for transluminal delivery and a deployed orientation configured to anchor within the left atrial appendage and fluidically isolate the left atrial appendage from a left atrium, a recessed socket accessible from the left atrium through an opening, and a closure covering the opening; and
 a modular active element configured for implantation and detachable engagement within the recessed socket of the docking station, and
(b) a delivery catheter to transluminally deliver the modular active element to the recessed socket of the docking station, in which the modular active element is configured for detachable coupling to the delivery catheter,
in which the modular active element comprises a capacitor paired with an inductor to provide a first LC circuit, in which the modular active element optionally comprises a second LC circuit positioned external to the modular active element adapted to provide a magnetic flux to power the first LC circuit.

14. A system comprising:
(a) a device for implantation in a left atrial appendage of a heart, the device comprising a docking station comprising:
 (i) a radially expansible element that is adjustable between a contracted orientation suitable for transluminal delivery and a deployed orientation configured to anchor within the left atrial appendage and fluidically isolate the left atrial appendage (LAA) from a left atrium;
 (ii) a recessed socket accessible from the left atrium through an opening; and
 (iii) a closure covering the opening;
(b) a modular active element configured for implantation and detachable engagement within the recessed socket of the docking station; and
(c) a delivery catheter to transluminally deliver the modular active element to the recessed socket of the docking station, in which the modular active element is configured for detachable coupling to the delivery catheter, and
in which the modular active element is configured to sit within the recessed socket and comprises a sensing device comprising a proximal sensing part that extends into the left atrium when the modular active element is implanted in the recessed socket, the sensing device configured to sense a pressure of the left atrium and to wirelessly transmit a detected signal to a processor, and
in which the modular active element comprises a radially expansible anchor configured to deploy distally of the recessed socket when the modular active element is engaged within the recessed socket to anchor the modular active element in the recessed socket.

15. The system according to claim 14, in which the modular active element comprises an inductor.

16. The system according to claim 14, in which the sensing device comprises a charging coil that is configured to relay data sensed by the sensing device to a remote receiver.

17. The system according to claim 14, in which the modular active element comprises a radially expansible anchor configured to anchor the modular active element in the recessed socket.

18. A system comprising:
(a) a device for implantation in a left atrial appendage of a heart, the device comprising a docking station comprising:
 (i) a radially expansible element that is adjustable between a contracted orientation suitable for transluminal delivery and a deployed orientation configured to anchor within the left atrial appendage and fluidically isolate the left atrial appendage (LAA) from a left atrium;
 (ii) a recessed socket accessible from the left atrium through an opening; and
 (iii) a closure covering the opening;
(b) a modular active element configured for delivery to the recessed socket of the docking station; and
(c) a delivery catheter to transluminally deliver the modular active element to the recessed socket of the docking station, wherein:
 the modular active element comprises a sensing device having a distal part that is disposed distally of the recessed socket when the modular active element is engaged within the recessed socket, and
 in which the modular active element is configured to remain attached to the delivery catheter during use.

19. The system according to claim 18, wherein the radially expansible element comprises a tissue ablation device.

* * * * *

UNITED STATES PATENT AND TRADEMARK OFFICE
CERTIFICATE OF CORRECTION

PATENT NO. : 12,167,855 B2
APPLICATION NO. : 17/284333
DATED : December 17, 2024
INVENTOR(S) : Tony O'Halloran and John Thompson Page 1 of 1

It is certified that error appears in the above-identified patent and that said Letters Patent is hereby corrected as shown below:

In the Specification

Column 1, Line 10 Delete "18/199,970.7," and insert --18199970.7,--.

Signed and Sealed this
Twenty-first Day of January, 2025

Coke Morgan Stewart
*Acting Director of the United States Patent and Trademark Office*